US011008606B2

(12) United States Patent
Wigler et al.

(10) Patent No.: US 11,008,606 B2
(45) Date of Patent: May 18, 2021

(54) RANDOM NUCLEOTIDE MUTATION FOR NUCLEOTIDE TEMPLATE COUNTING AND ASSEMBLY

(71) Applicants: Michael Wigler, Cold Spring Harbor, NY (US); Dan Levy, Merrick, NY (US)

(72) Inventors: Michael Wigler, Cold Spring Harbor, NY (US); Dan Levy, Merrick, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 544 days.

(21) Appl. No.: 15/515,913

(22) PCT Filed: Oct. 9, 2015

(86) PCT No.: PCT/US2015/054981
§ 371 (c)(1),
(2) Date: Mar. 30, 2017

(87) PCT Pub. No.: WO2016/057947
PCT Pub. Date: Apr. 14, 2016

(65) Prior Publication Data
US 2017/0306392 A1    Oct. 26, 2017

Related U.S. Application Data

(60) Provisional application No. 62/062,571, filed on Oct. 10, 2014.

(51) Int. Cl.
*C12Q 1/6827* (2018.01)
*C12Q 1/6851* (2018.01)
*C12Q 1/6869* (2018.01)
*C07H 21/04* (2006.01)
*C12N 15/10* (2006.01)

(52) U.S. Cl.
CPC .......... *C12Q 1/6827* (2013.01); *C07H 21/04* (2013.01); *C12N 15/102* (2013.01); *C12N 15/1031* (2013.01); *C12N 15/1058* (2013.01); *C12Q 1/6851* (2013.01); *C12Q 1/6869* (2013.01); *C12Q 2521/539* (2013.01); *C12Q 2525/161* (2013.01); *C12Q 2531/113* (2013.01); *C12Q 2535/122* (2013.01)

(58) Field of Classification Search
CPC .................................................... C12Q 1/6827
USPC ......................................................... 506/26
See application file for complete search history.

(56) References Cited

U.S. PATENT DOCUMENTS

| 7,799,531 B2 | 9/2010 | Mitchell | |
|---|---|---|---|
| 8,399,195 B2 | 3/2013 | Mitchell | |
| 8,877,442 B2 | 11/2014 | Quake | |
| 2004/0076982 A1* | 4/2004 | Gokarn | C12N 9/0004 |
| | | | 435/6.12 |
| 2005/0266453 A1 | 12/2005 | Coia et al. | |
| 2007/0154892 A1* | 7/2007 | Wain-Hobson | C12P 19/34 |
| | | | 435/6.14 |
| 2007/0258954 A1* | 11/2007 | Iverson | C07K 14/245 |
| | | | 424/93.4 |
| 2009/0047680 A1 | 2/2009 | Lok | |
| 2013/0079231 A1 | 3/2013 | Pushkarev et al. | |
| 2013/0338043 A1 | 12/2013 | Firnberg et al. | |
| 2014/0065609 A1 | 3/2014 | Hicks et al. | |
| 2014/0066317 A1 | 3/2014 | Talasaz | |
| 2014/0173777 A1* | 6/2014 | Puri | C12N 15/8247 |
| | | | 800/281 |
| 2014/0377762 A1 | 12/2014 | Kelly et al. | |
| 2018/0201973 A1* | 7/2018 | Nauwelaers | B01L 7/525 |

FOREIGN PATENT DOCUMENTS

| WO | WO 2004/042078 A1 | 5/2004 |
|---|---|---|
| WO | WO 2013/177086 A1 | 11/2013 |
| WO | WO 2014/013218 A1 | 1/2014 |

OTHER PUBLICATIONS

Notification of Transmittal of the International Search Report and the Written Opinion of the International Searching Authority; or the Declaration, including an International Search Report and Written Opinion of the International Searching Authority, dated Feb. 1, 2016 in connection with PCT International Application No. PCT/US2015/054981, filed Oct. 9, 2015.

Notification Concerning Transmittal of International Preliminary Report on Patentability (Chapter I of the Patent Cooperation Treaty), including an International Preliminary Report on Patentability and Written Opinion of the International Searching Authority, dated Apr. 20, 2017 by The International Bureau of WIPO in connection with PCT International Application No. PCT/US2015/054981, filed Oct. 9, 2015.

(Continued)

*Primary Examiner* — Karla A Dines
(74) *Attorney, Agent, or Firm* — Gary J. Gershik

(57) ABSTRACT

A method for determining the number of nucleic acid molecules (NAMs) in a group of NAMs, comprising
i) obtaining an amplified and mutagenized group of NAMs that was produced by
   a. subjecting the group of NAMs to a chemical mutagenesis which mutates only select nucleic acid bases in the group of NAMs at a rate of 10% to 90% thus forming a group of mutagenized NAMs (mNAMs), and
   b. amplifying the group of mNAMs;
ii) obtaining sequences of the mNAMs in the group of amplified mNAMs; and
iii) counting the number of different sequences obtained in step (ii) to determine the number of unique mNAMs in the group of mNAMS,
thereby determining the number of NAMs in the group of NAMs.

6 Claims, 13 Drawing Sheets
Specification includes a Sequence Listing.

(56) References Cited

OTHER PUBLICATIONS

Casbon, J. A. et al. (2011) "A method for counting PCR template molecules with application to next generation sequencing," Nucleic Acids Res 39(12): 1-8.
Fu, G. K. et al. (2011) "Counting individual DNA molecules by the stochastic attachment of diverse labels," Proc. Natl. Acad. Sci. U.S.A. 108(22): 9026-9031.
Kumar, V. and Levy, D. (2015) "Clustering by transitive propagation," arXiv: 1506.0372v1 [cs.LG]: 1-19.
Levy, D. and Wigler, M. (2014) "Facilitated sequence counting and assembly by temptate mutagenesis," Proc. Natl. Acad. Sci. U.S.A. 111(43): E4832-E4637.
Ni, X. et al. (2013) "Reproducible copy number variation patterns among single circulating tumor cells of lung cancer patients," Proc. Natl. Acad. Sci. U.S.A. 110(52): 21083-21088.
Smallwood, S. A. et al. (2014) "Single-cell genome-wide bisulfite sequencing for assessing epigenetic heterogeneity," Nature Methods 11(8): 817-820.
Voskoboynik, A. et al. (2013) "The genome sequence of the colonial chordate, *Botryllus schlosseri*," eLife 2(e00569): 1-24.
"MethylEasy™ Xceed Rapid Sodium Bisulphite Modification Kit" User Guide, Human Genetic Signatures Pty Ltd. 1-23.
May 15, 2017 Communication Pursuant to Article 161(2) and 162 EPC issued in connection with corresponding European Application No. 15849374.2.
Nov. 27, 2017 Response to Communication Pursuant to Article 161(2) and 162 EPC filed in connection with corresponding European Application No. 15849374.2.
Feb. 21, 2018 Extended European Search Report issued in connection with corresponding European Application No. 15849374.2.
Grunau, C., Clark, S. J., & Rosenthal, A. (2001). Bisulfite genomic sequencing: systematic investigation of critical experimental parameters. Nucleic acids research, 29(13), e65-e65.
Sep. 19, 2018 Response to Extended European Search Report filed in connection with corresponding European Application No. 15849374.2.
Mar. 28, 2019 Communication Pursuant to Article 94(3) EPC issued in connection with corresponding European Application No. 15849374.2.
Aug. 6, 2019 Response to Communication Pursuant to Article 94(3) EPC filed in connection with corresponding European Application No. 15849374.2.
Oct. 25, 2019 Communication Pursuant to Article 94(3) EPC issued in connection with corresponding European Application No. 15849374.2.
Mar. 29, 2020 Office Action issued in connection with corresponding Israeli Application No. 251509.
May 4, 2020 Response to Communication Pursuant to Article 94(3) EPC filed in connection with corresponding European Application No. 15849374.2.

* cited by examiner

RANDOM NUCLEOTIDE MUTATION FOR NUCLEOTIDE TEMPLATE COUNTING AND ASSEMBLY

This application is a § 371 national stage of PCT International Application No. PCT/US2015/054981, filed Oct. 9, 2015, claiming benefit of U.S. Provisional Application No. 62/062,571, filed Oct. 10, 2014, the contents of each of which are hereby incorporated by reference into the application.

Throughout this application, various publications are referenced, including referenced in parenthesis. Full citations for publications referenced in parenthesis may be found listed at the end of the specification immediately preceding the claims. The disclosures of all referenced publications in their entireties are hereby incorporated by reference into this application in order to more fully describe the state of the art to which this invention pertains.

REFERENCE TO SEQUENCE LISTING

This application incorporates-by-reference nucleotide sequences which are present in the file named "180213_86434-A-PCT-US_Sequence_Listing_ADR.txt" which is 2 kilobytes in size, and which was created Feb. 13, 2018 in the IBM-PC machine format, having an operating system compatibility with MS-Windows, which is contained in the text file filed Feb. 14, 2018.

BACKGROUND OF INVENTION

Despite improvements in DNA sequencing, many problems of interpretation arise when trying to count or assemble molecules (templates) that are largely identical. Some problems in genomic analysis have remained difficult despite the development of high throughput sequencing methods. Many of these problems arise from the inability to distinguish identical and nearly identical template sequences. Counting molecules of identical composition in an RNA sequencing assay or the copy number of identical stretches of DNA currently depend on quantitative methods that adjust imperfectly for the distortions of data caused by sample processing.

Moreover, when read lengths are short, determining the physical connection of distinguishable elements separated by long identical stretches is difficult to impossible and limits the ability to phase single nucleotide variants (SNVs), identify transcript isoforms, and assemble through repetitive genomic regions.

There are several protocols in which a sequence of random nucleotides is appended to the template molecules before amplification and sequencing. This methodology has been applied under a variety of names to identify PCR duplicates (McCloskey et al., 2007; Miner et al., 2004), improve counting of DNA (Casbon et al., 2011; Fu et al., 2011) and RNA (Islam et al., 2014; Jabara et al., 2011; Kivioja et al., 2012) templates, and reduce sequence error (Hiatt et al., 2013; Kinde et al., 2011; Schmitt et al., 2012). Each implementation has its own name for the random nucleotide sequences, which can be referred to as varietal tags (Schmitt et al., 2012). Each implementation also has its own shortcoming.

SUMMARY OF THE INVENTION

The present invention provides a method is provided for determining the number of nucleic acid molecules (NAMs) in a group of NAMs, comprising i) obtaining an amplified and mutagenized group of NAMs that was produced by
   a) subjecting the group of NAMs to a chemical mutagenesis which mutates only select nucleic acid bases in the group of NAMs at a rate of 10% to 90% thus forming a group of mutagenized NAMs (mNAMs), and
   b) amplifying the group of mNAMs;
ii) obtaining sequences of the mNAMs in the group of amplified mNAMs; and
iii) counting the number of different sequences obtained in step (ii) to determine the number of unique mNAMs in the group of mNAMS, thereby determining the number of NAMs in the group of NAMs.

The present invention also provides a method for determining the number of nucleic acid molecules (NAMs) in a group of NAMs, comprising i) subjecting the group of NAMs to a chemical mutagenesis which mutates only select nucleic acid bases in the group of NAMs at a rate of 10% to 90%, to produce a group of mutagenized NAMs (mNAMs);
ii) amplifying the group of mNAMs;
iii) sequencing the mNAMs in the group of amplified mNAMs to obtain sequences of the mNAMs; and
iv) counting the number of different sequences obtained in step (iii) to determine the number of unique mNAMs in the group of mNAMs, thereby determining the number of NAMs in the group of NAMs.

The present invention also provides a method for determining the number of different sequences in a group of nucleic acid molecules (NAMs) that have been mutagenized and then amplified comprising a) obtaining the group of NAMs that have been mutagenized and then amplified;
b) obtaining sequences of the mutagenized NAMs (mNAMs) in the group of amplified mNAMs; and
c) counting the number of different sequences obtained in step (ii), thereby determining the number of different sequences in the group of amplified mNAMs.

The present invention also provides a method for sequencing a nucleic acid molecule (NAM) that comprises two or more segments having substantially the same sequence, and that has a length of more than one sequencing read, comprising i) obtaining two or more copies of the NAM;
ii) subjecting each copy of the NAM in step (i) to a mutagenesis that mutates only select nucleic acid bases in the NAMs at a rate of 10% to 90% to produce mutated copies of the NAM (mcNAM);
iii) amplifying each of the mcNAMs;
iv) obtaining composite sequences of the mcNAMs that are produced by assembling sequence reads of the amplified mcNAMs, such that when taken together, span as much as possible of the entire length of the NAM, by
   a) aligning the sequence reads according to matching mutation patterns in overlaps of the sequence reads, and
   b) mapping the composite sequences, thereby sequencing the NAM.

The present invention also provides a method for determining genomic copy number information from genomic material, comprising, i) obtaining segments of the genomic material; and
ii) determining the number of segments of the genomic material according to the method of the claimed invention, thereby determining genomic copy number information from genomic material.

The present invention also provides a method for profiling RNA transcripts, comprising
i) obtaining a group of RNA transcripts;
ii) determining the number of RNA transcripts in the group of RNA transcripts according to the method of the claimed invention; and
iii) determining the proportionate number of a plurality of RNA transcripts having the same sequence to a second different plurality of RNA transcripts that have the same sequence, thereby determining RNA transcript profile.

The present invention also provides a method for determining allelic imbalance, comprising
i) obtaining copy number of a first allele;
ii) obtaining copy number of a second allele; and
iii) comparing the copy numbers obtained in steps (i) and (ii), thereby determining allelic imbalance, wherein the copy number in steps (i) and (ii) is obtained by the method of the claimed invention.

The present invention also provides a method for determining genome assembly, comprising
i) obtaining segments of a genome, wherein the segments span the entire length of the genome;
ii) sequencing the segments of the genome according to the method of the claimed invention;
iii) aligning the sequences obtained in step (ii) according to matching mutation patterns in overlaps of the sequences; and
iv) mapping the sequences, thereby assembling the genome.

The present invention also provides a method for determining haplotype assembly, comprising
i) obtaining a group of alleles, wherein the alleles in the group of alleles are located in the same chromosome;
ii) sequencing each allele in the group of alleles according to the method of the claimed invention, and
iii) comparing the sequences obtained in step (ii), thereby determining haplotype assembly.

The present invention also provides a kit for determining the number of NAMs in a group of NAMs comprising:
a) a mutagen; and
b) instructions for performing mutagenesis resulting in suboptimal mutagenesis, wherein the mutagen is a bisulfite or a salt thereof, or a deamination agent.

The present invention also provides a composition of matter comprising a plurality of mutagenized nucleic acid molecules (mNAMs), wherein selected mutable nucleic acid positions in the plurality of mutagenized NAMs (mNAMs) are mutated at a rate of 10% to 90%.

The present invention also provides a composition of matter derived from sequencing primers has the sequence: ACACTCTTTCCCTACACACGACGCTCTTCCGATC*T (SEQ ID NO:1), wherein the cytosines (C) are methylated, and wherein *T is a phosphorothioated thymine.

The present invention also provides a composition of matter derived from sequencing primers has the sequence: 5Phos-GATCGGAAGAGCGGTTCAGCAGGAATGCCGA*G (SEQ ID NO:2), wherein the cytosines (C) are methylated, wherein *G is a phosphorothioated guanine, and wherein 5Phos is a 5'-phosphorylated, deoxyuridine-containing anchor-primer.

The present invention also provides a composition of matter comprising two or more copies of a nucleic acid molecule (NAM) comprising two or more segments having substantially the same sequence, and that has a length of more than one sequencing read, wherein each copy of the NAM has a unique primer at its 5' end and another unique primer at its 3' end, and is subjected to a mutagenesis that mutates each mutable position in the NAMs at a rate of 10% to 90% to produce mutated copies of the NAM (mcNAM), wherein the unique primers of each mcNAM lack a nucleotide that is mutable by the mutagenesis.

The present invention also provides sequence information produced by a system including one or more processing units which counts the number of different sequences obtained by a sequencer that processed the group of amplified mNAMs in the method of the present invention, or the group of mcNAMs of in the method of the present invention.

The present invention also provides a system including one or more processing units which counts the number of different sequences obtained by a sequencer that processed the group of amplified mNAMs of in the method of the present invention, or the group of mcNAMs of in the method of the present invention.

Illustration of the process of counting indistinguishable template molecules (panel A). In the first step, the molecules were mutated by random process, creating a unique mutation signature to each molecule (panel B). Cytidine deamination is also illustrated. Cytidine deamination is a mutational method that converts cytidine (underlined) to a uridine (bold). Upon amplification, uridine becomes a thymidine (bold) (panel C). The sequenced nucleotide strings are aligned, aggregated by their mutational patterns (panel D), and the number of the distinct patterns counted.

Figure 2:
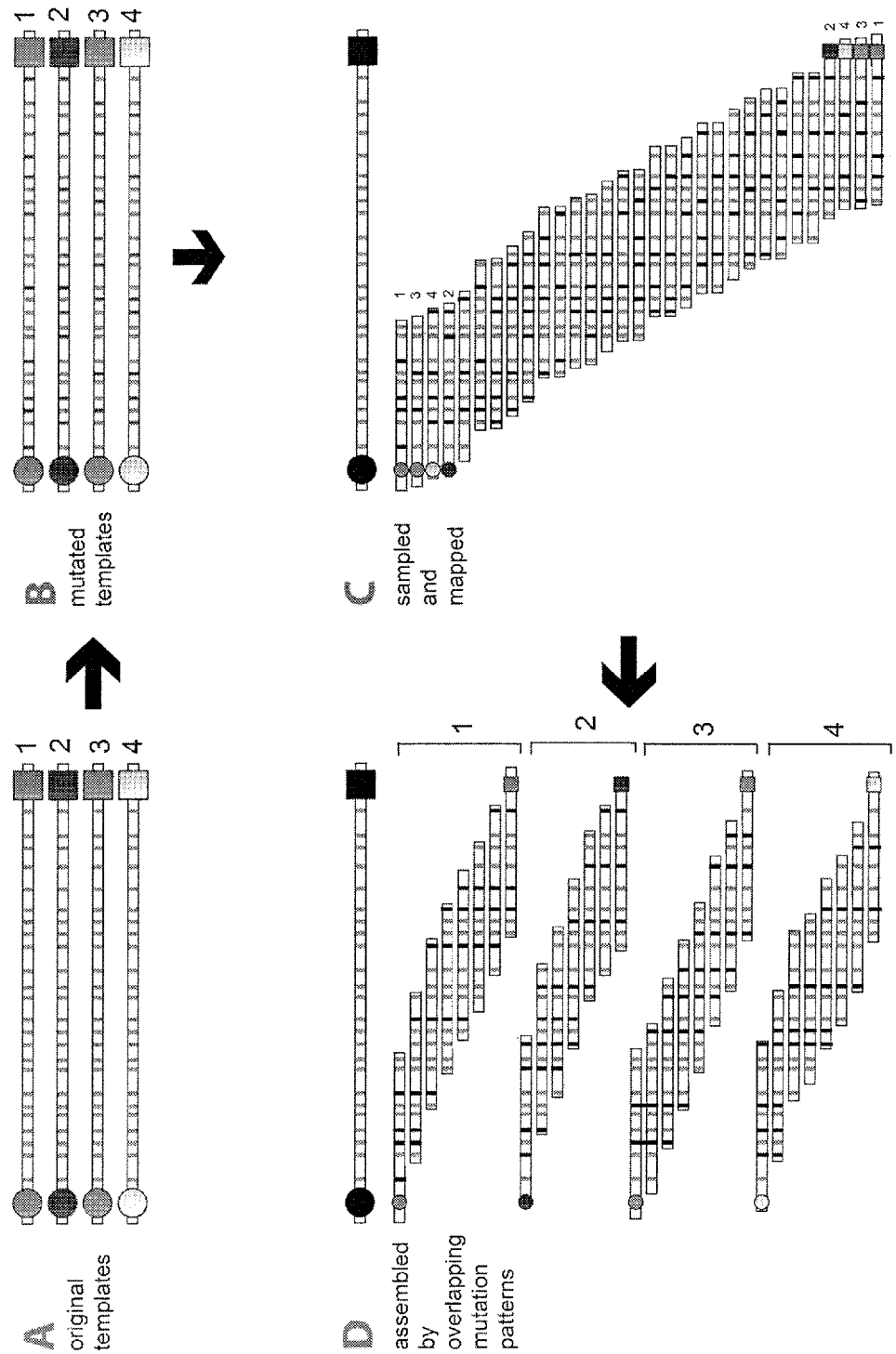

FIG. 2. Assembling Long Templates

Illustration of the process of connecting distinguishable markers separated by a long span of indistinguishable sequence. In this example, each template has a unique pair of markers, or "end tags", denoted by the colored circle and square (panel A). Markers of the same color occur on the same template strands and are said to be "in phase". Gray marks on the templates show positions that may mutate. Each template was subjected to a random mutation process (panel B) that converts some of the positions (converted positions shown in black). After amplification and sequencing, each read is mapped to the reference template (panel C, top strand). Finally, by matching mutation patterns from overlapping reads, the phase of the original templates was recovered (panel D).

Figure 3:
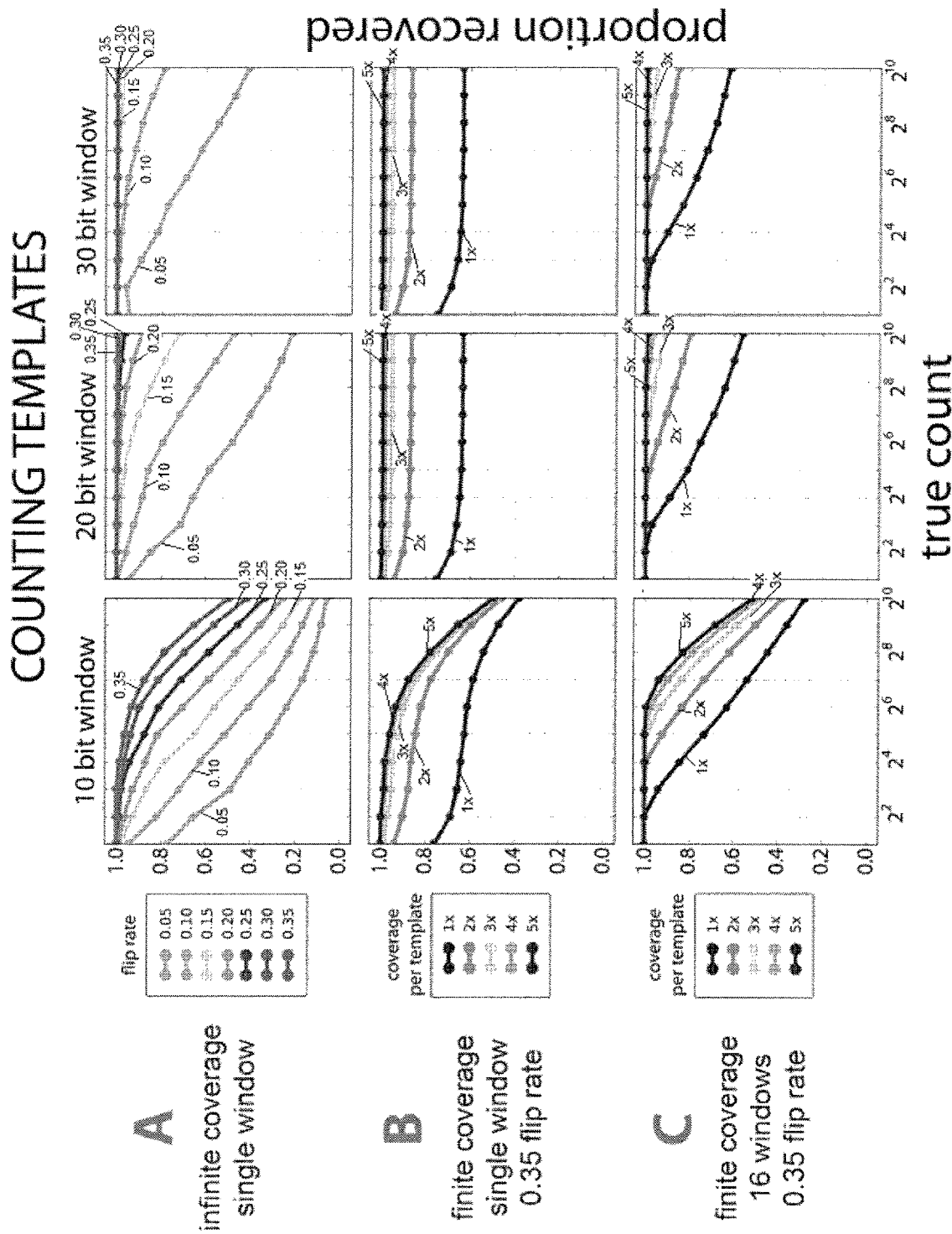

FIG. 3. Recovering Counts

The ability to recover the template count is a function of the window size, template length, flip rate, number of templates, and depth of coverage. Simulation results of template count estimation are shown under a variety of conditions. Each panel has three plots, for window sizes of 10, 20, and 30 bits. The x axis shows the true count from 2 to 1,024 ($\log_2$ scale) and the y axis shows the average estimated count divided by the true count, or the proportion of templates recovered. Panel A simulates recovery when the template is one window long for a range of flip rates for infinite coverage. Panel B shows the results from one window template under finite coverage (1× to 5× reads per template) for a fixed flip rate of 0.35. Panel C repeats the results of panel B for long templates comprised of 16 read lengths.

Figure 4:
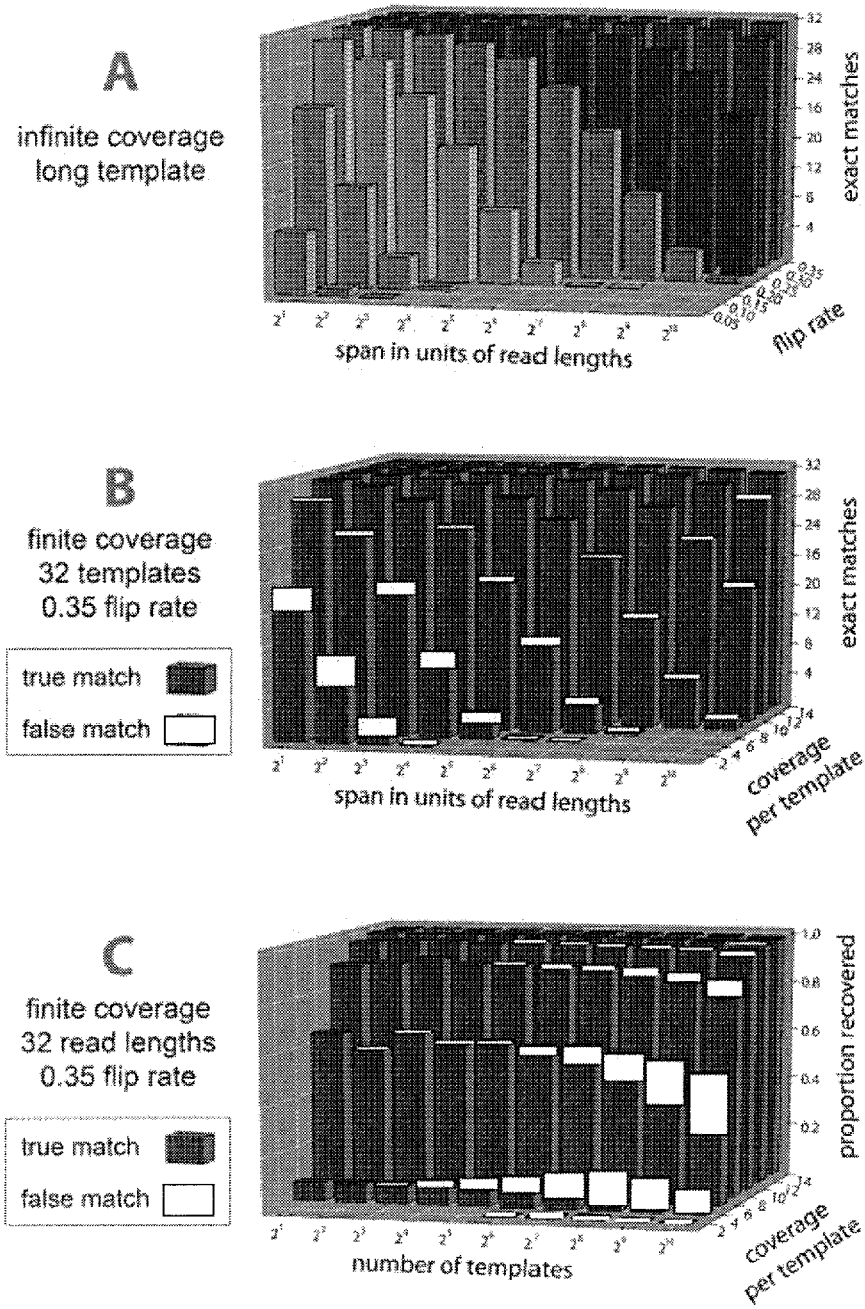

FIG. 4. Recovering Phase

Proper phasing of end tags separated by a long span of identical sequence depends on window size, template length, flip rate, number of templates, and depth of coverage. In panels A and B, simulation results are shown for the recovery of phase for 32 templates across a span ranging from 2 to 1,024 read lengths for a 30-bit window. In panel A, infinite coverage was assumed and recovery was examined as a function of flip rate. Because coverage is exhaustive and the assembly graph is well characterized, there are no errors and all phased results are correct. In panels B and C, the case of finite coverage was considered, fixing the flip rate at 0.35 over a range of coverages from 2× to 14× per template. In panel B, the number of template molecules was fixed at 32 to explore the effect of template length on recovery of phase. In panel C, the template length was fixed to 32 read lengths to explore the effect of the number of templates. Because not every read is observed, a greedy algorithm was used that may return exact matches that are correct (black) or incorrect (white).

Figure 5:
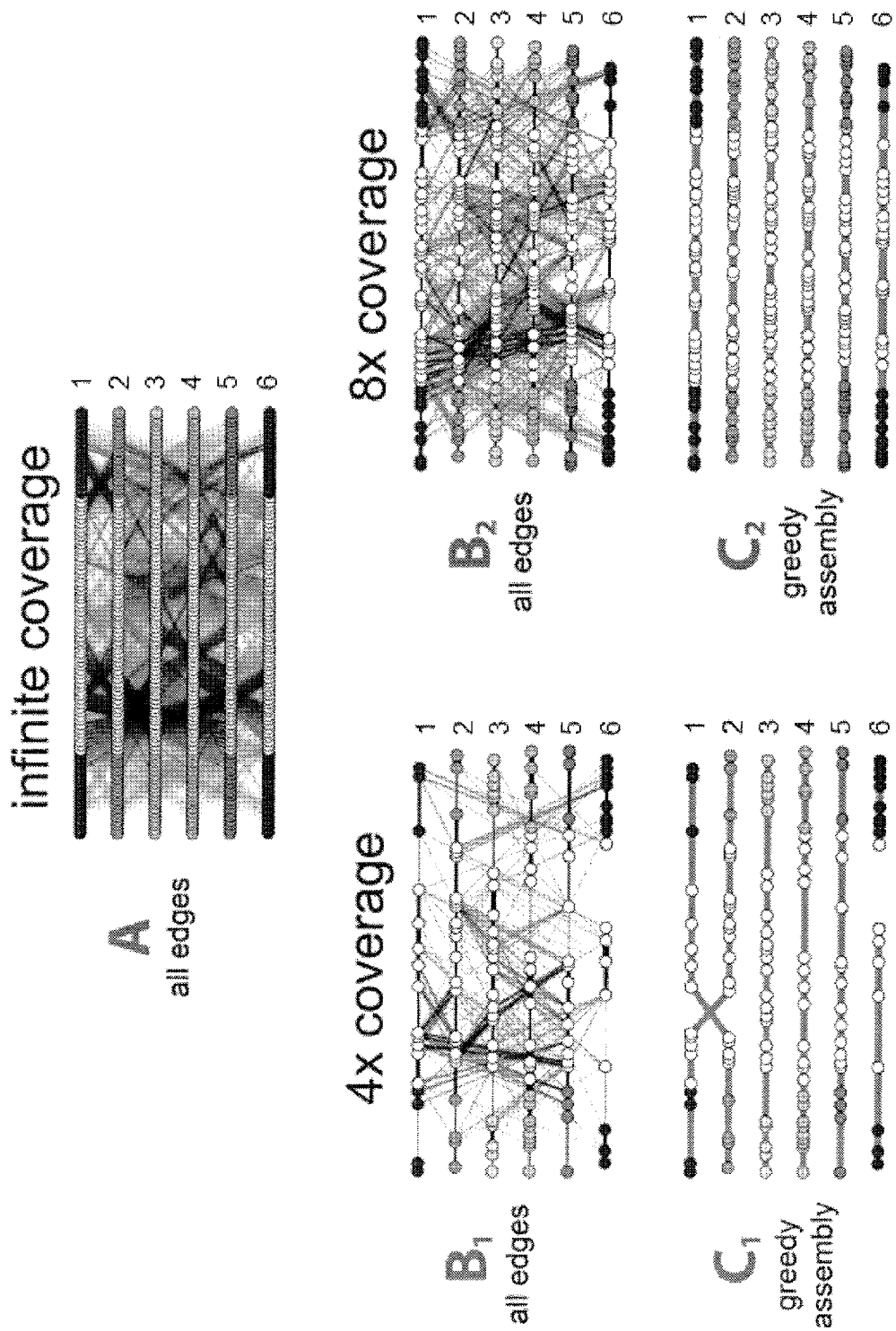

FIG. 5. Greedy Path Assembly

To carry out the pattern assembly shown in FIG. 2, a graph was defined in which each read is vertex. Some reads contain their end tag (colored circles) and some do not (white circles). Two reads with an edge were connected if they agree on their overlap. The weight of an edge reflects the strength of that overlap. Panel A depicts the template information assuming exhaustive coverage, drawing all distinct reads and the edges between them. In panels $B_1$ and $B_2$, sample reads were finitely sampled from the templates at a depth of coverage of 4× and 8× per template, respectively. From this information the greedy algorithm was applied (panels $C_1$ and $C_2$), to select the best edges, shown in red. When coverage is low (panel $C_1$), some paths do not succeed in spanning the length of the template and of those that do, three determine the correct phasing, and two are in error. Under higher coverage (panel $C_2$), all paths span the template and all six are correctly phased.

Figure 6:
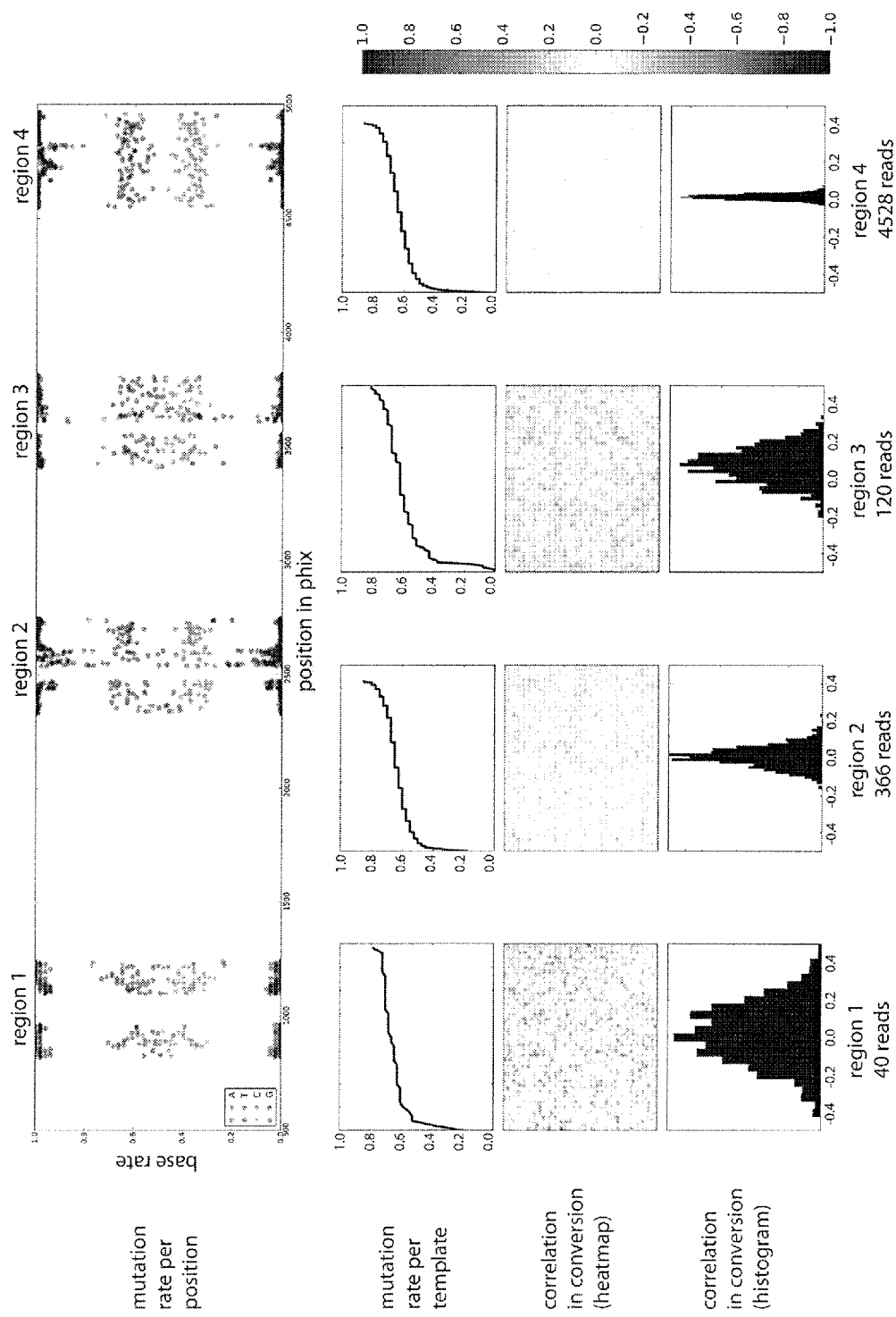

FIG. 6. Partial Bisulfite Mutagenesis of a PhiX Template Genome

The experimental results from partial bisulfite mutagenesis of a phix template genome. Panel A depicts the rate at which each base is observed over all the data for those positions with a coverage of at least 30 reads. Panel B depicts the cumulative distribution of the conversion rate per read. Panel C depicts the correlation in flips for all cytosines in the targeted region. Panel D depicts panel C as a histogram. For the best amplified position, partial conversion was determined with a 60% flip rate randomly distributed throughout each read.

Figure 7:
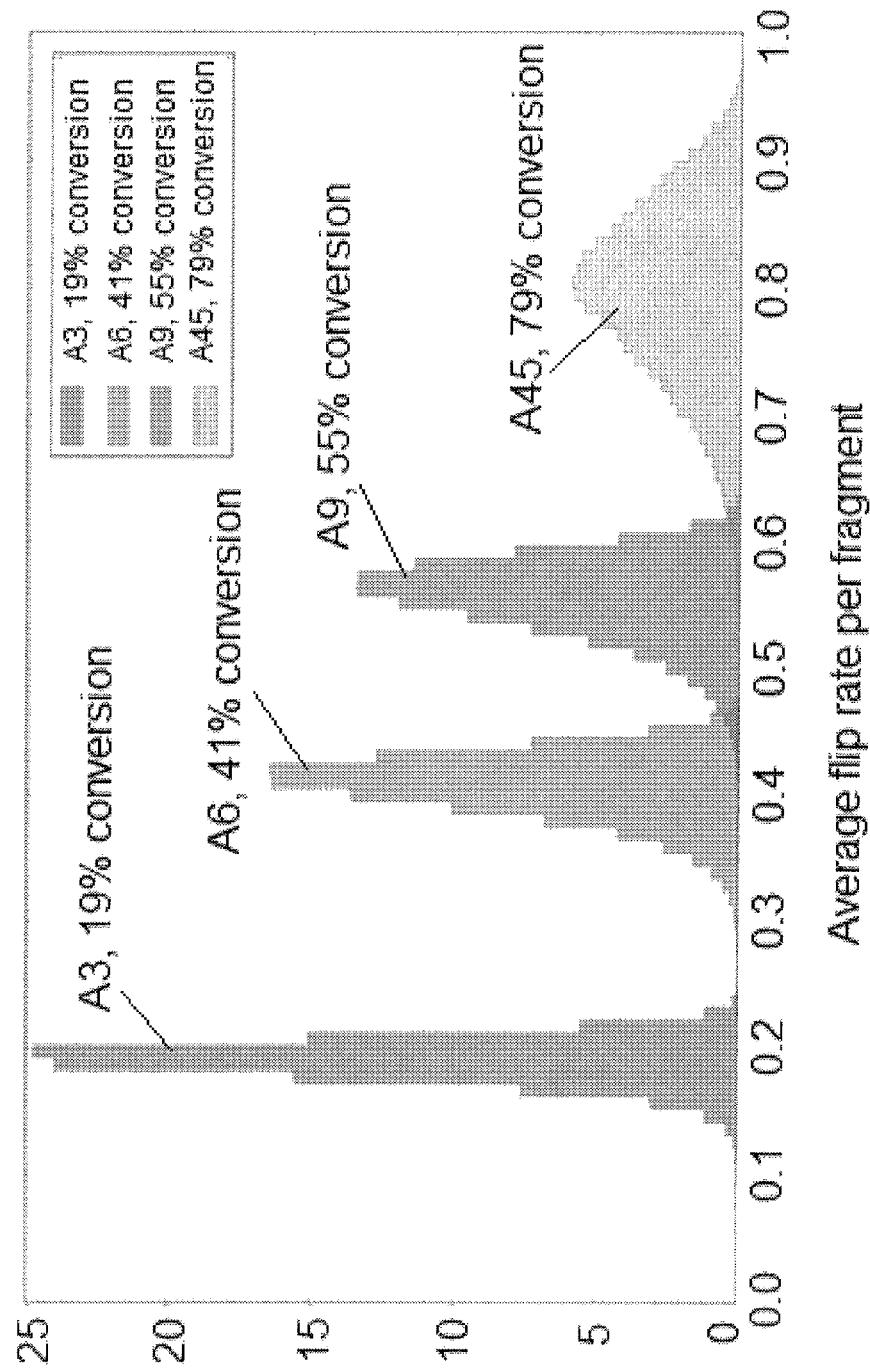

FIG. 7. Conversion rate as a function of incubation time and temperature. The datasets A3, A6, A9 and A45 are the 3, 6, 9 and 45 minute conversions described herein.

Figure 8:
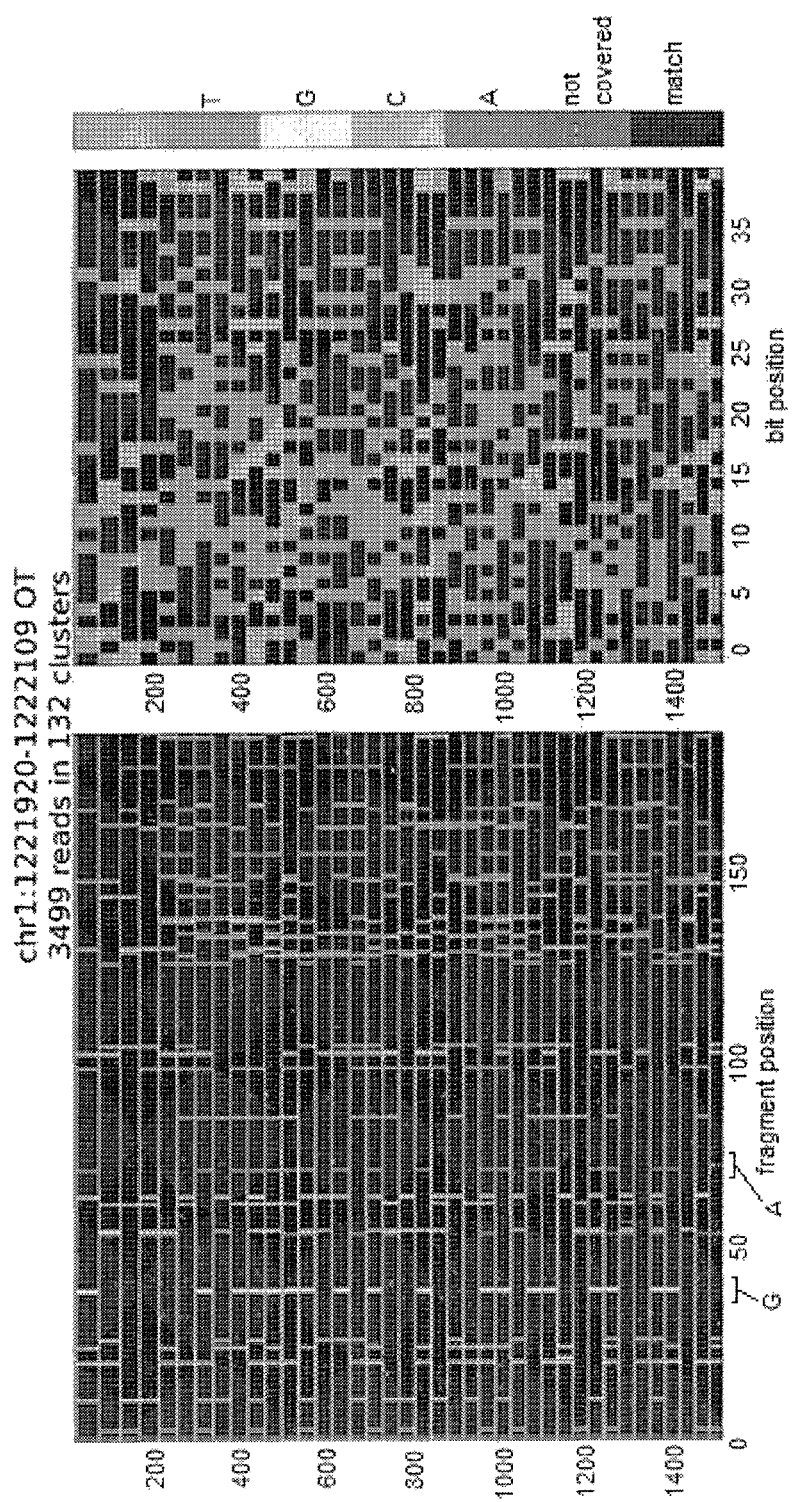

FIG. 8. Subset of clustered reads showing mutational patterns and two heterozygous positions in the sample. The panel on the left shows all the positions in the fragment while the plot on the right shows only cytosine (bit) positions. The white lines separate reads derived from the same initial template. Each cluster contains between 30 and 50 reads. Black indicates a position where the read matches the reference genome. The frequent gray squares are cytosines that have converted to thymine. The white and light grey streaks are linked heterozygous alleles which split according to mutation pattern. Sparse background errors are typically from the sequencer while the bands of error are typically the result of PCR.

Figure 9:
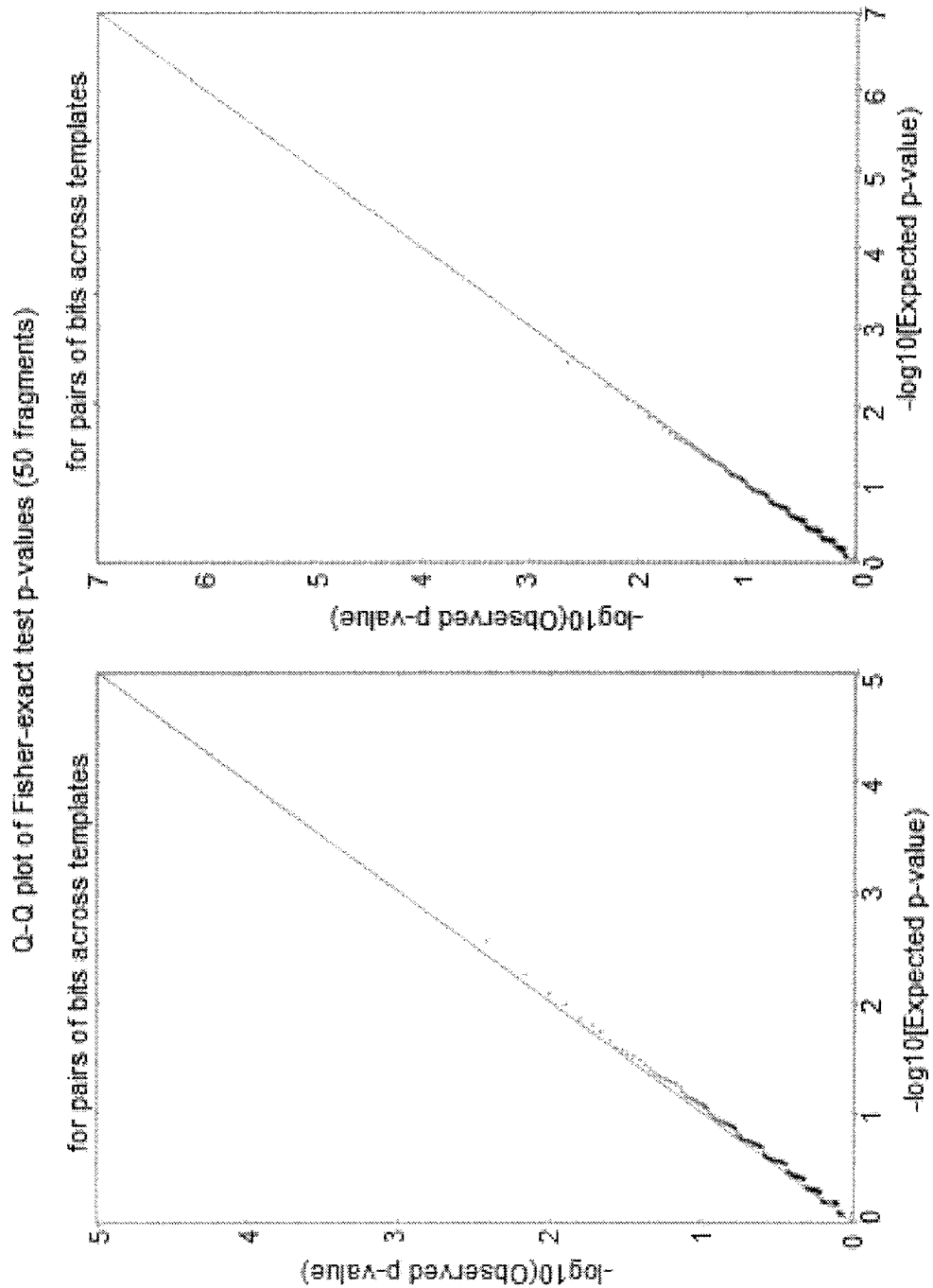

FIG. 9. Bit positions and bit patterns are uncorrelated. For the plot on the left, pairs of positions (100,000) were sampled and the Fisher exact p-value computed to test the independence of bits by position. For the plot on the right, pairs of templates (100,000) were sampled and the Fisher exact p-value computed to test the independence of bits within a pattern. Both plots conform to the expected distribution.

Figure 10:
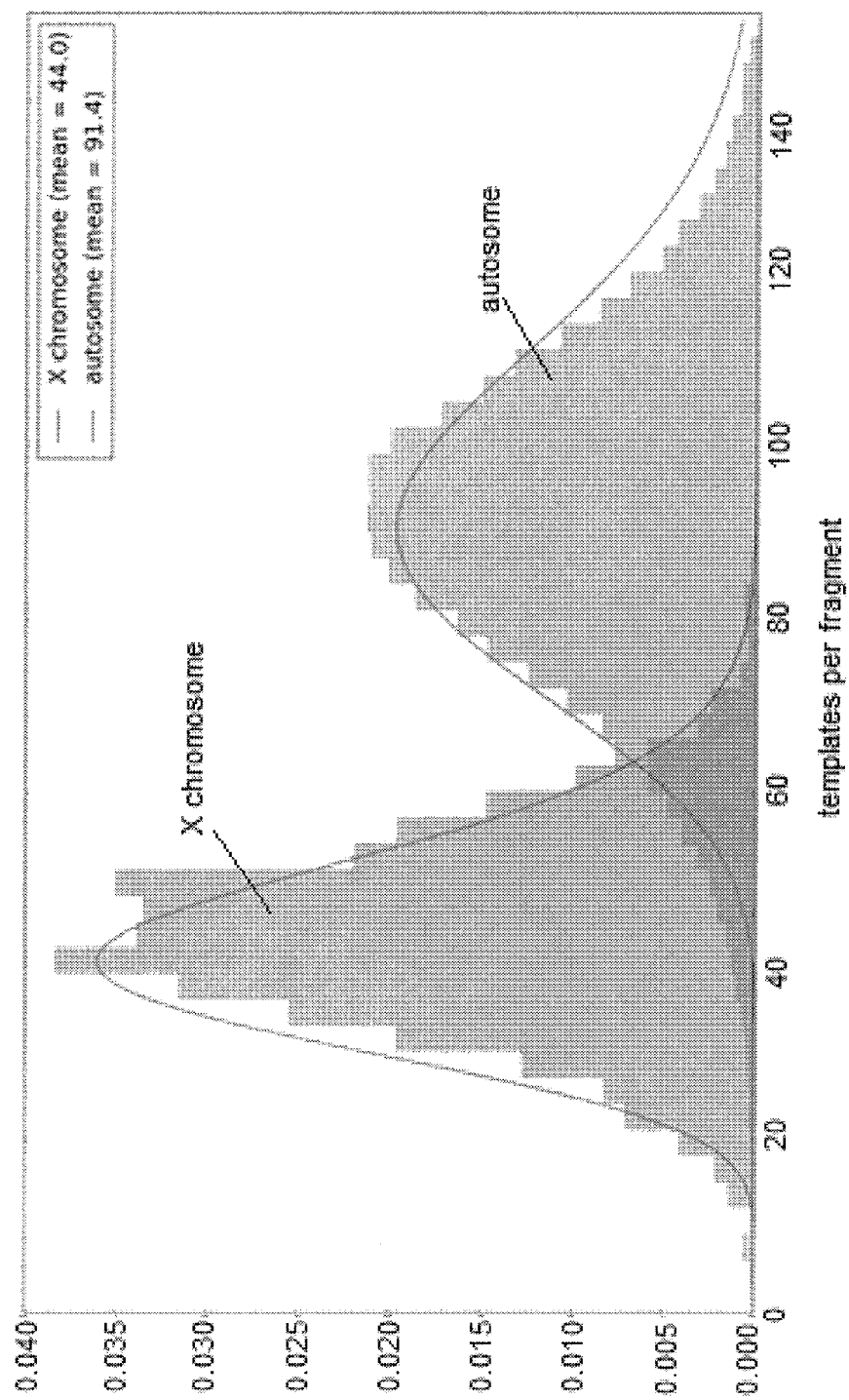

FIG. 10. Comparison of template count distributions for fragments from the autosome and X chromosome. Since the sample is male, 2 to 1 ratio was observed in the mean template counts. The histogram is the empirical distribution and the curve shows a negative binomial fit.

Figure 11:
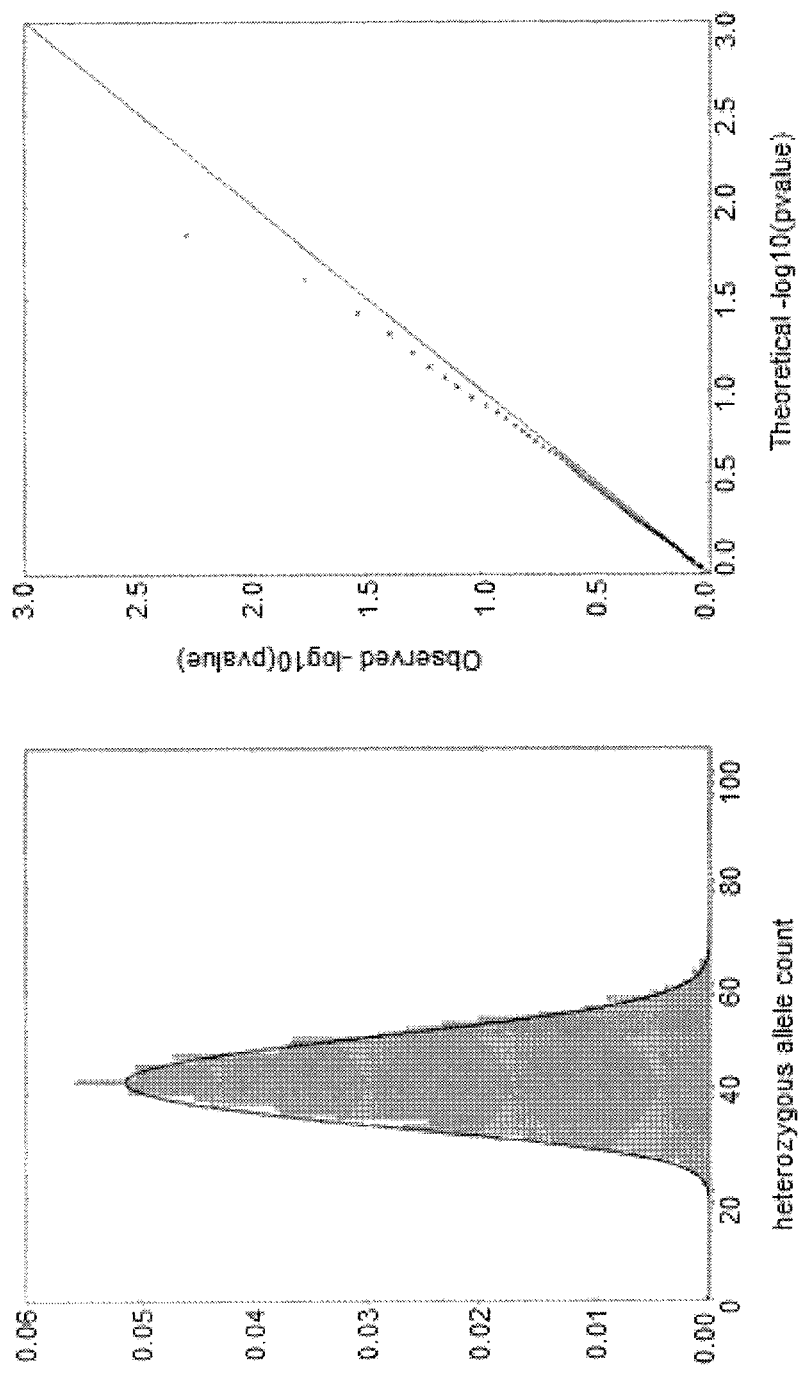

FIG. 11. Heterozygous allele counts by template demonstrate perfect fit to the binomial distribution. The plot on the left shows as a histogram the counts for one allele. The curve shows the theoretical expectation of the count distribution assuming a binomial distribution for the allele at each locus assuming the given locus coverage. The plot on the right shows the Q-Q plot over all 6000 heterozygous positions observed.

Figure 12:
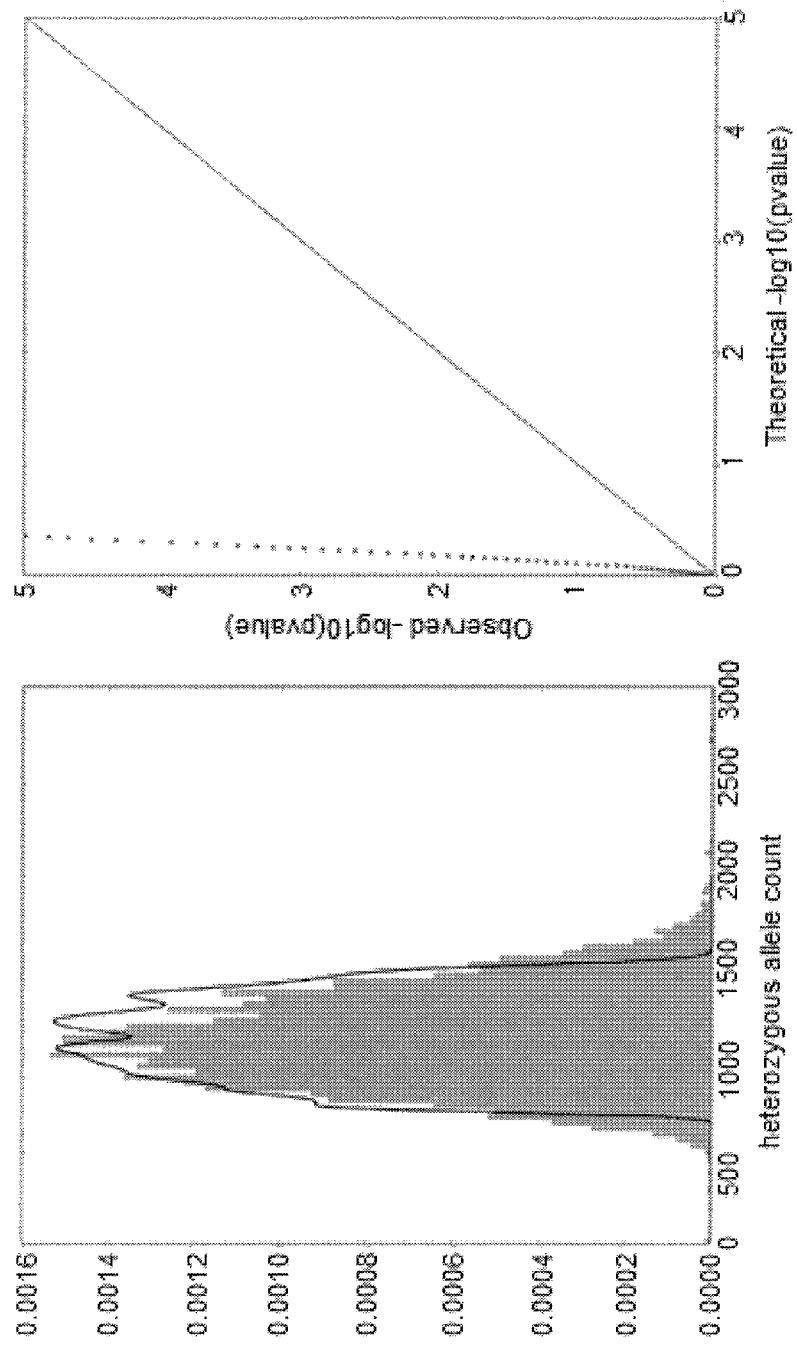

FIG. 12. Heterozygous allele counts by read fail to fit binomial distribution. As shown in FIG. 11, except the fit is quite poor. Far better to count templates than reads.

Figure 13:
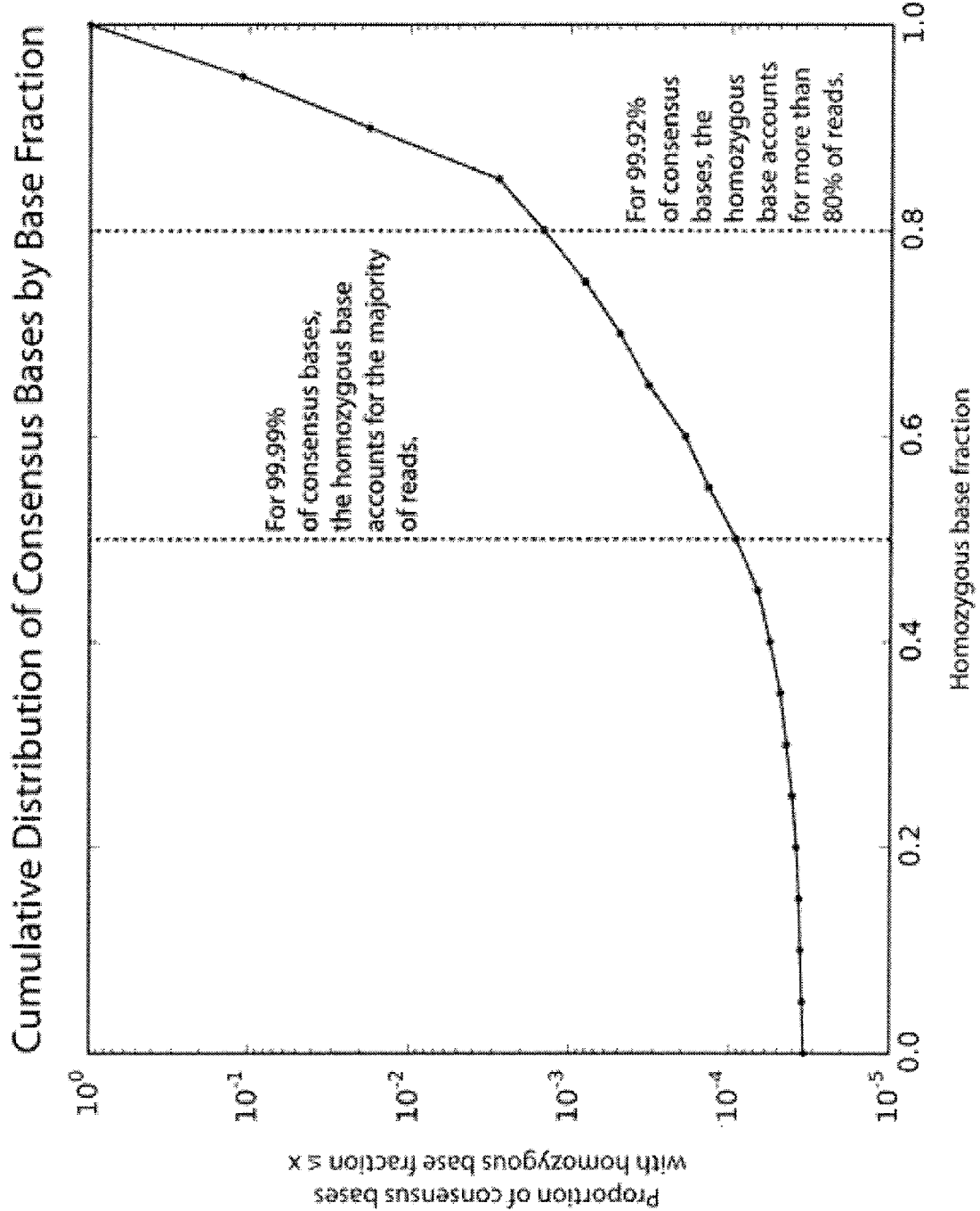

FIG. 13. Properties of the consensus sequences derived by clustering reads with the same mutation pattern. For each consensus sequence base, the proportion of reads reporting the homozygous base was determined. These error rates are order of magnitude below sequencer error.

DETAILED DESCRIPTION OF THE INVENTION

The present invention provides a method for determining the number of nucleic acid molecules (NAMs) in a group of NAMs, comprising
  i) obtaining an amplified and mutagenized group of NAMs that was produced by
    a) subjecting the group of NAMs to a chemical mutagenesis which mutates only select nucleic acid bases in the group of NAMs at a rate of 10% to 90% thus forming a group of mutagenized NAMs (mNAMs), and
    b) amplifying the group of mNAMs;
  ii) obtaining sequences of the mNAMs in the group of amplified mNAMs; and
  iii) counting the number of different sequences obtained in step (ii) to determine the number of unique mNAMs in the group of mNAMS,
thereby determining the number of NAMs in the group of NAMs.

The present invention provides a method for determining the number of nucleic acid molecules (NAMs) in a group of NAMs, comprising
  i) obtaining an amplified and mutagenized group of NAMs that was produced by
    a) subjecting the group of NAMs to a chemical mutagenesis which mutates only select nucleic acid positions in the group of NAMs at a rate of 10% to 90% thus forming a group of mutagenized NAMs (mNAMs), and
    b) amplifying the group of mNAMs;

ii) obtaining sequences of the mNAMs in the group of amplified mNAMs; and iii) counting the number of different sequences obtained in step (ii) to determine the number of unique mNAMs in the group of mNAMS, thereby determining the number of NAMs in the group of NAMs.

In some embodiments, obtaining sequences comprises obtaining composite sequences produced by assembling sequence reads of the mNAMs by a) aligning the sequence reads according to matching mutation patterns in overlaps of the sequence reads, thereby obtaining composite sequences, and b) mapping the composite sequences; and wherein counting the number of jointly overlapping different composite sequences obtained.

In some embodiments, obtaining sequences in comprises obtaining composite sequences produced by assembling sequence reads of the mNAMs by a) aligning the sequence reads according to matching mutation patterns in overlaps of the sequence reads, thereby obtaining composite sequences, and b) mapping the composite sequences; and wherein counting the number of different composite sequences obtained.

The present invention also provides a method for determining the number of nucleic acid molecules (NAMs) in a group of NAMs, comprising i) subjecting the group of NAMs to a chemical mutagenesis which mutates only select nucleic acid bases in the group of NAMs at a rate of 10% to 90%, to produce a group of mutagenized NAMs (mNAMs);

ii) amplifying the group of mNAMs;

iii) sequencing the mNAMs in the group of amplified mNAMs to obtain sequences of the mNAMs; and iv) counting the number of different sequences obtained in step (iii) to determine the number of unique mNAMs in the group of mNAMs, thereby determining the number of NAMs in the group of NAMs.

The present invention also provides a method for determining the number of nucleic acid molecules (NAMs) in a group of NAMs, comprising i) subjecting the group of NAMs to a chemical mutagenesis which mutates only select nucleic acid positions in the group of NAMs at a rate of 10% to 90%, to produce a group of mutagenized NAMs (mNAMs);

ii) amplifying the group of mNAMs;

iii) sequencing the mNAMs in the group of amplified mNAMs to obtain sequences of the mNAMs; and iv) counting the number of different sequences obtained in step (iii) to determine the number of unique mNAMs in the group of mNAMs, thereby determining the number of NAMs in the group of NAMs.

In some embodiments, the sequencing comprises assembling sequence reads of the mNAMs into composite sequences by a) aligning the sequence reads according to matching mutation patterns in overlaps of the sequence reads, thereby obtaining composite sequences, and b) mapping the composite sequences; and wherein counting the number of jointly overlapping different composite sequences obtained.

In some embodiments, the sequencing comprises assembling sequence reads of the mNAMs into composite sequences by a) aligning the sequence reads according to matching mutation patterns in overlaps of the sequence reads, thereby obtaining composite sequences, and b) mapping the composite sequences; and wherein counting the number of different composite sequences obtained in step (iii).

In one or more embodiments, a sub-group of NAMs in the group of NAMs is determined to have substantially the same nucleotide sequence.

In one or more embodiments, the sub-group of NAMs is determined to have nucleotide sequences that are at least 95, 96, 97, 98, 99, 99.1, 99.2, 99.3, 99.4, 99.5, 99.6, 99.7, 99.9, or 99.9% identical.

In one or more embodiments, the nucleotide sequences of a sub-group of NAMs comprise a stretch of consecutive nucleotides having a sequence which includes at least two mutable positions and is i) identical to the sequence of a stretch of consecutive nucleotides within another NAM within the sub-group of NAMs, or ii) determined to have at least 95, 96, 97, 98, 99, 99.1, 99.2, 99.3, 99.4, 99.5, 99.6, 99.7, 99.9, or 99.9% identical to the sequence of a stretch of consecutive nucleotides within another NAM within the sub-group of NAMs.

In one or more embodiments, the counting comprises counting the number of different sequences that are determined to have substantially the same sequence except for their mutable positions, thereby determining the number of NAMs in the group of NAMs that had substantially the same sequence.

In one or more embodiments, the counting comprises counting the number of different sequences which lack substantially the same sequence in any stretch including at least two mutable positions, thereby determining the number of NAMs without substantially the same sequence in the group of NAMs.

The present invention also provides a method for determining the number of different sequences in a group of nucleic acid molecules (NAMs) that have been mutagenized and then amplified comprising a) obtaining the group of NAMs that have been mutagenized and then amplified;

b) obtaining sequences of the mutagenized NAMs (mNAMs) in the group of amplified mNAMs; and c) counting the number of different sequences obtained in step (ii), thereby determining the number of different sequences in the group of amplified mNAMs.

The present invention also provides a method for sequencing a nucleic acid molecule (NAM) that comprises two or more segments having substantially the same sequence, and that has a length of more than one sequencing read, comprising i) obtaining two or more copies of the NAM;

ii) subjecting each copy of the NAM in step (i) to a mutagenesis that mutates only select nucleic acid positions in the NAMs at a rate of 10% to 90% to produce mutated copies of the NAM (mcNAM);

iii) amplifying each of the mcNAMs;

iv) obtaining composite sequences of the mcNAMs that are produced by assembling sequence reads of the amplified mcNAMs, such that when taken together, span as much as possible of the entire length of the NAM, by a) aligning the sequence reads according to matching mutation patterns in overlaps of the sequence reads, and b) mapping the composite sequences, thereby sequencing the NAM.

In some embodiments, a copy of the NAM is a partial copy of the NAM.

In some embodiments, a copy of the NAM has at least 50 bp of identical or complementary sequence to the NAM.

In some embodiments, a copy of the NAM is a complete copy of the NAM.

The present invention also provides a method for sequencing a nucleic acid molecule (NAM) that comprises two or more segments having substantially the same sequence, and that has a length of more than one sequencing read, comprising
  i) obtaining two or more copies of the NAM;
  ii) subjecting each copy of the NAM in step (i) to a mutagenesis that mutates only select nucleic acid bases in the NAMs at a rate of 10% to 90% to produce mutated copies of the NAM (mcNAM);
  iii) amplifying each of the mcNAMs;
  iv) obtaining composite sequences of the mcNAMs that are produced by assembling sequence reads of the amplified mcNAMs, such that when taken together, span as much as possible of the entire length of the NAM, by
    a) aligning the sequence reads according to matching mutation patterns in overlaps of the sequence reads, and
    b) mapping the composite sequences,
thereby sequencing the NAM.

The present invention also provides a method for sequencing a nucleic acid molecule (NAM) that comprises two or more segments having substantially the same sequence, and that has a length of more than one sequencing read, comprising
  i) obtaining two or more copies of the NAM;
  ii) subjecting each copy of the NAM in step (i) to a chemical mutagenesis that mutates only select nucleic acid bases in the NAMs at a rate of 10% to 90% to produce mutated copies of the NAM (mcNAM);
  iii) amplifying each of the mcNAMs;
  iv) obtaining composite sequences of the mcNAMs that are produced by assembling sequence reads of the amplified mcNAMs, such that when taken together, span as much as possible of the entire length of the NAM, by
    a) aligning the sequence reads according to matching mutation patterns in overlaps of the sequence reads, and
    b) mapping the composite sequences,
thereby sequencing the NAM.

In some embodiments, each of the two or more copies of the NAM has a unique primer at its 5' end and another unique primer at its 3' end.

In some embodiments, the unique primers of each mcNAM lack a nucleotide that is mutable by the mutagenesis.

The present invention also provides a method for determining genomic copy number information from genomic material, comprising,
  i) obtaining segments of the genomic material; and
  ii) determining the number of segments of the genomic material according to the method of the present invention,
thereby determining genomic copy number information from genomic material.

The present invention also provides a method for profiling RNA transcripts, comprising
  i) obtaining a group of RNA transcripts;
  ii) determining the number of RNA transcripts in the group of RNA transcripts according to the method of the claimed invention; and
  iii) determining the proportionate number of a plurality of RNA transcripts having the same sequence to a second different plurality of RNA transcripts that have the same sequence,
thereby determining RNA transcript profile.

The present invention also provides a method for determining allelic imbalance, comprising
  i) obtaining copy number of a first allele;
  ii) obtaining copy number of a second allele; and
  iii) comparing the copy numbers obtained in steps (i) and (ii),
thereby determining allelic imbalance, wherein the copy number in steps (i) and (ii) is obtained by the method of the present invention.

The present invention also provides a method for determining genome assembly, comprising
  i) obtaining segments of a genome, wherein the segments span the entire length of the genome;
  ii) sequencing the segments of the genome according to the method of the claimed invention;
  iii) aligning the sequences obtained in step (ii) according to matching mutation patterns in overlaps of the sequences; and
  iv) mapping the sequences,
thereby assembling the genome.

The present invention also provides a method for determining haplotype assembly, comprising
  i) obtaining a group of alleles, wherein the alleles in the group of alleles are located in the same chromosome;
  ii) sequencing each allele in the group of alleles according to the method of the claimed invention, and
  iii) comparing the sequences obtained in step (ii),
thereby determining haplotype assembly.

In one or more embodiments, the rate of mutagenizing each mutable position of the NAMs in the group of NAMs is 25% to 75%.

In one or more embodiments, the rate of mutagenizing each mutable position of the NAMs in the group of NAMs is 40% to 60%.

In one or more embodiments, the rate of mutagenizing each mutable position of the NAMs in the group of NAMs is 50%.

In one or more embodiments, the proportion of all bases mutated in each mNAM is about 3% to 30%.

In one or more embodiments, the mutagenesis is by cytosine deamination.

In one or more embodiments, the mutagenesis is performed after binding template molecules to a bead or surface.

In one or more embodiments, biotinylated primers are attached to templates.

In one or more embodiments, templates linked to biotinylated moieties are attached to streptavidin beads.

In one or more embodiments, the mutagenesis further comprises beads and/or varietal tags.

In some embodiments, the cytosine deamination is induced by a bisulfite or a salt thereof.

In some embodiments, the cytosine deamination is induced by enzymology.

In some embodiments, the cytosine deamination is induced by an activation-induced deaminase.

In one or more embodiments, the mutagenesis comprises contacting the group of NAMs with a depurination agent, transposase agent, or an alkylating agent.

In one or more embodiments, each mutable position of the NAMs comprises a cytosine (C).

In one or more embodiments, the cytosine (C) is mutated to a uracil (U) or a thymine (T).

In one or more embodiments, each NAM in the group of NAMs has a unique primer at its 5' end and another unique primer at its 3' end.

In one or more embodiments, the primer comprises one or more methylated cytosines.

In one or more embodiments, the primer comprises one or more phosphorothioated nucleotide bases.

In one or more embodiments, the primer further comprises a 5'-phosphorylated, deoxyuridine-containing anchor-primer.

In one or more embodiments, the primer has the sequence: ACACTCTTTCCCTACACACGACGCTCTTCCGATCT (SEQ ID NO:3).

In one or more embodiments, the primer has the sequence: ACACTCTTTCCCTACACACGACGCTCTTCCGATC*T (SEQ ID NO:1), wherein the cytosines (C) are methylated, and wherein *T is a phosphorothioated thymine.

In one or more embodiments, the cytosines (C) are methylated.

In one or more embodiments, the primer has the sequence: GATCGGAAGAGCGGTTCAGCAGGAATGCCGAG (SEQ ID NO:4)

In one or more embodiments, the primer further comprises a 5'-phosphorylated, deoxyuridine-containing anchor-primer.

In one or more embodiments, the primer has the sequence: having the sequence: GATCGGAAGAGCGGTTCAGCAGGAATGCCGA*G (SEQ ID NO:2), wherein the cytosines (C) are methylated, wherein *G is a phosphorothioated guanine, and wherein 5Phos is a 5'-phosphorylated, deoxyuridine-containing anchor-primer.

In one or more embodiments, the cytosines (C) are methylated.

In one or more embodiments, the assembling further comprises aligning the sequences according to unique primers at the 5' and 3' ends.

In one or more embodiments, the sequence of each unique primer comprises a segment that is substantially the same sequence, and an amplification primer that is complementary to the shared sequence when amplifying the mNAMs or copy thereof.

In some embodiments, amplification is performed using a sequence-specific "wobble" primer.

In one or more embodiments, each unique primer comprises a unique tag sequence.

In one or more embodiments, the method further comprises the step of tagging each NAM or copy thereof.

In one or more embodiments, the tag lacks a nucleotide that is mutable by the mutagenesis.

In one or more embodiments, the NAM is within a mixture of DNA or

RNA extracted from a cell.

In some embodiments, the DNA or RNA extracted from the cell has been fragmented.

In some embodiments, the DNA or RNA extracted from the cell has been fragmented by mechanical shearing or one or more restriction enzymes.

In one or more embodiments, the one or more restriction enzyme is PstI.

In one or more embodiments, fragmentation occurs before amplifying.

In one or more embodiments, fragmentation occurs after amplifying.

In one or more embodiments, fragmentation occurs after mutagenesis.

In one or more embodiments, the method of the claimed invention further comprises subjecting the fragmented DNA or RNA to end-repair.

In one or more embodiments, the method of the claimed invention further comprises subjecting the fragmented DNA or RNA to adenylation.

In one or more embodiments, the method of the claimed invention further comprises subjecting the fragmented DNA or RNA to ligation with methyl-cytosine adaptors, wherein the methyl-cytosine adaptors are bisulfite resistant sequencing adaptors.

In one or more embodiments, the NAM is a DNA molecule.

In some embodiments, the DNA molecule is a fragment of genomic DNA.

In one or more embodiments, the DNA molecule is a cDNA molecule.

In one or more embodiments, the NAM is an RNA molecule.

In one or more embodiments, the RNA molecule is an mRNA molecule.

In one or more embodiments, the RNA molecule is a viral RNA molecule.

In one or more embodiments, the NAM is an RNA molecule derived from one or more cell lines.

In one or more embodiments, the method of the claimed invention further comprises reverse transcription of the NAM.

In one or more embodiments, the reverse transcription is with poly-T and methyl-cytosines, wherein the methyl-cytosines are resistant to bisulfite mutation.

In one or more embodiments, chemical mutagenesis occurs prior to reverse transcription.

In one or more embodiments, one or more NAMs in the group of NAMs has a length of one sequencing read length.

In one or more embodiments, one or more NAMs in the group of NAMs has a length of two or more sequencing read lengths.

In one or more embodiments, the sequencing read length is 2, 3, 4, 5, 6, 7, 8, 9, 10, or 10-3000 sequencing read lengths.

In one or more embodiments, the number of NAMs in the group of NAMs is about 2, 3, 4, 5, 6, 7, 8, 9, 10, or 10-10000.

In one or more embodiments, the number of NAMs in the group of NAMs is greater than 10000, then diluting the group of NAMs.

In one or more embodiments, diluting the group of NAMs to comprise 1000 or more NAMs in the group of NAMs.

In one or more embodiments, the amplifying is by short-range or long-range polymerase chain reaction (PCR).

In one or more embodiments, the mutagen of the mutagenesis is diluted.

In one or more embodiments, the group of NAMs is incubated with a mutagen at an incubation temperature of about 70 to 78 degrees Celsius.

In one or more embodiments, the incubation temperature is about 73 degrees Celsius.

In one or more embodiments, the group of NAMs is incubated with a mutagen at an incubation time of about 3 to 45 minutes.

In one or more embodiments, the group of NAMs is incubated with a mutagen at an incubation time of about 5 to 20 minutes.

In one or more embodiments, the incubation time is about 3, 6, or 9 minutes.

In one or more embodiments, the incubation time is about 10 minutes.

The present invention also provides a kit for determining the number of NAMs in a group of NAMs comprising:
a) a mutagen; and
b) instructions for performing mutagenesis resulting in suboptimal mutagenesis, wherein the mutagen is a bisulfite or a salt thereof, or a deamination agent.

In some embodiments, the bisulfite or salt thereof is $NaHSO_3$.

In one or more embodiments, the mutagen induces cytosine deamination.

In one or more embodiments, the cytosine deamination is by enzymology.

In one or more embodiments, the mutagen is diluted.

In one or more embodiments, the kit of the present invention further comprises a plurality of unique primers including:
a) a plurality of substantially unique primers suitable for ligation to the 5' of a NAM; and
b) a plurality of substantially unique primers suitable for ligation to the 3' of a NAM.

wherein the substantially unique primers comprise substantially unique tags.

In one or more embodiments, the kit of the present invention further comprises a DNA polymerase having 3'-5' proofreading activity.

In one or more embodiments, the plurality of substantially unique primers comprises $10^n$ primers, wherein n is an integer from 2 to 9.

In one or more embodiments, the substantially unique tags are at least 6 nucleotides long.

In one or more embodiments, the substantially unique tags are at least 15 nucleotides long.

In one or more embodiments, the substantially unique primers comprise sets of substantially unique primers having shared sample tags.

In one or more embodiments, the sample tags are at least 2 or 4 nucleotides long.

In one or more embodiments, the sequence of the substantially unique tag is not altered by the mutagen.

In one or more embodiments, the kit of the present invention further comprises a primer wherein the cytosines (C) are methylated.

In one or more embodiments, the methylated primer having the sequence: ACACTCTTTCCCTACACACGACGCTCTTCCGATC*T (SEQ ID NO:1), wherein the cytosines (C) are methylated, and wherein *T is a phosphorothioated thymine.

In one or more embodiments, the methylated primer having the sequence: 5Phos-GATCGGAAGAGCGGTTCAGCAGGAATGCCGA*G (SEQ ID NO:2), wherein the cytosines (C) are methylated, wherein *G is a phosphorothioated guanine, and wherein 5Phos is a 5'-phosphorylated, deoxyuridine-containing anchor-primer.

The present invention also provides a composition of matter comprising a plurality of mutagenized nucleic acid molecules (mNAMs), wherein selected mutable nucleic acid positions in the plurality of mutagenized NAMs (mNAMs) are mutated at a rate of 10% to 90%.

In one or more embodiments, each mutable position is mutated at a rate of 25% to 75%.

In one or more embodiments, each mutable position is mutated at a rate of 40% to 60%.

In one or more embodiments, each mutable position is mutated at a rate of 50%.

In one or more embodiments, each mutable nucleic acid base is mutated at a rate of 25% to 75%.

In one or more embodiments, each mutable nucleic acid base is mutated at a rate of 40% to 60%.

In one or more embodiments, each mutable nucleic acid base is mutated at a rate of 50%.

In one or more embodiments, the proportion of all nucleic acids mutated in each mNAM is about 3% to 30%.

In one or more embodiments, the mutable nucleic acid position is a cytosine position of the mNAMs and the mutagenesis is deamination of the cytosine.

In one or more embodiments, the mutable nucleic acid base is a cytosine base of the mNAMs and the mutagenesis is deamination of the cytosine.

In one or more embodiments, the deamination of the cytosine is induced by a bisulfite or a salt thereof.

In one or more embodiments, the cytosine deamination of the cytosine is induced by enzymology.

In one or more embodiments, the cytosine deamination of the cytosine is induced by an activation-induced deaminase.

In one or more embodiments, the mutable nucleic acid position is mutagenized by contacting the group of NAMs with a depurination agent, transposase agent, or an alkylating agent.

In one or more embodiments, each mutable position of the NAMs comprises a cytosine (C).

In one or more embodiments, the cytosine (C) is mutated to a uracil (U) or a thymine (T).

In one or more embodiments, each NAM in the plurality of NAMs has a unique primer at its 5' end and another unique primer at its 3' end.

In one or more embodiments, the primer comprises one or more methylated cytosines.

In one or more embodiments, the primer comprises one or more phosphorothioated nucleotide bases.

In one or more embodiments, the primer further comprises a 5'-phosphorylated, deoxyuridine-containing anchor-primer.

In one or more embodiments, the primer has the sequence: ACACTCTTTCCCTACACACGACGCTCTTCCGATCT (SEQ ID NO:3).

In one or more embodiments, the plurality of mNAMS bearing a primer wherein the sequence of the primer is: ACACTCTTTCCCTACACACGACGCTCTTCCGATC*T (SEQ ID NO:1), and wherein *T is a phosphorothioated thymine.

In one or more embodiments, the cytosines (C) are methylated.

In one or more embodiments, all the cytosines (C) are methylated.

In one or more embodiments, the primer has the sequence: GATCGGAAGAGCGGTTCAGCAGGAATGCCGAG (SEQ ID NO:4).

In one or more embodiments, the primer further comprises a 5'-phosphorylated, deoxyuridine-containing anchor-primer.

In one or more embodiments, the plurality of mNAMS bearing a primer wherein the sequence of the primer is: 5Phos-GATCGGAAGAGCGGTTCAGCAGGAATGCCGA*G (SEQ ID NO:2), wherein *G is a phosphorothioated guanine, and wherein 5Phos is a 5'-phosphorylated, deoxyuridine-containing anchor-primer.

In one or more embodiments, the cytosines (C) are methylated.

The present invention also provides a composition of matter derived from sequencing primers has the sequence: ACACTCTTTCCCTACACACGACGCTCTTCCGATC*T (SEQ ID NO:1), wherein the cytosines (C) are methylated, and wherein *T is a phosphorothioated thymine.

The present invention also provides a composition of matter derived from sequencing primers has the sequence: 5Phos-GATCGGAAGAGCGGTTCAGCAGGAATGCCGA*G (SEQ ID NO:2), wherein the cytosines (C) are methylated, wherein *G is a phosphorothioated guanine, and wherein 5Phos is a 5'-phosphorylated, deoxyuridine-containing anchor-primer.

The present invention also provides a composition of matter comprising two or more copies of a nucleic acid molecule (NAM) comprising two or more segments having substantially the same sequence, and that has a length of more than one sequencing read, wherein each copy of the NAM has a unique primer at its 5' end and another unique primer at its 3' end, and is subjected to a mutagenesis that mutates each mutable position in the NAMs at a rate of 10% to 90% to produce mutated copies of the NAM (mcNAM), wherein the unique primers of each mcNAM lack a nucleotide that is mutable by the mutagenesis.

The present invention also provides sequence information produced by a system including one or more processing units which counts the number of different sequences obtained by a sequencer that processed the group of amplified mNAMs in the method of the claimed invention, or the group of mcNAMs of in the method of the claimed invention.

The present invention also provides a system including one or more processing units which counts the number of different sequences obtained by a sequencer that processed the group of amplified mNAMs of in the method of the claimed invention, or the group of mcNAMs of in the method of the claimed invention.

The present invention also provides a method for sequencing a nucleic acid molecule (NAM) that comprises two or more segments having substantially the same sequence, and that has a length of more than one sequencing read, comprising
  i) obtaining two or more copies of the NAM;
  ii) subjecting each copy of the NAM in step (i) to a mutagenesis that mutates only select nucleic acid positions in the NAMs at a rate of 10% to 90% to produce mutated copies of the NAM (mcNAM);
  iii) amplifying each of the mcNAMs;
  iv) obtaining composite sequences of the mcNAMs that are produced by assembling sequence reads of the amplified mcNAMs, such that when taken together, span as much as possible of the entire length of the NAM, by de novo assembly,
thereby sequencing the NAM.

The present invention also provides a method for distinguishing between benign and malignantly transformed cells by detecting one or more single nucleotide polymorphisms (SNPs) in a sample from a subject and a reference sample from a control subject comprising a method of the claimed invention.

The present invention also provides a method for distinguishing between benign and malignantly transformed cells by detecting one or more single nucleotide polymorphisms (SNPs) in a first and second sample from a subject comprising a method of the claimed invention.

The present invention also provides a method for determining the presence of tumor cells in a sample by comparing a sample from a subject and a reference sample from a control subject comprising a method of the claimed invention.

The present invention also provides a method for determining the presence of tumor cells in a sample by comparing a first and second sample from a subject comprising a method of the claimed invention.

The present invention also provides a method for quantifying tumor cells in a sample by comparing a sample from a subject and a reference sample from a control subject comprising a method of the claimed invention.

The present invention also provides a method for quantifying tumor cells in a sample by comparing a sample from a first and second sample from a subject comprising a method of the claimed invention.

The present invention also provides a method for detecting one or more rare mutations by comparing a sample from a subject and a reference sample from a control subject comprising a method of the claimed invention.

The present invention also provides a method for detecting one or more rare mutations by comparing a sample from a first and second sample from a subject comprising a method of the claimed invention.

In one or more embodiments, the sample is a blood sample, plasma sample, serum sample, tissue sample, or cell sample.

In one or more embodiments, the tissue sample is from a tumor mass, surgically removed tumor mass, or margins of a surgically removed tumor mass.

The present invention also provides a method for detecting one or more rare mutations in a cell-free or substantially cell-free sample comprising a method of the claimed invention.

The present invention also provides a method for determining whether a fetus has at least one or more rare mutations in a cell-free or substantially cell-free sample comprising a method of the claimed invention In one or more embodiments, the sample is a maternal sample.

In one or more embodiments, the maternal sample is obtained from a member selected from: maternal blood, maternal plasma and maternal serum.

Each embodiment disclosed herein is contemplated as being applicable to each of the other disclosed embodiments. Thus, all combinations of the various elements described herein are within the scope of the invention.

It is understood that where a parameter range is provided, all integers within that range, and tenths thereof, are also provided by the invention. For example, "70 to 78 degrees Celsius" is a disclosure of 70.0 degrees Celsius, 70.1 degrees Celsius, 70.2 degrees Celsius, 70.3 degrees Celsius, 70.4 degrees Celsius, 70.5 degrees Celsius etc. up to 78.0 degrees Celsius.

Terms

Unless otherwise defined, all technical and scientific terms used herein have the same meaning as commonly understood by a person of ordinary skill in the art to which this invention belongs.

As used herein, and unless stated otherwise or required otherwise by context, each of the following terms shall have the definition set forth below.

As used herein, "about" in the context of a numerical value or range means ±10% of the numerical value or range recited or claimed, unless the context requires a more limited range.

The terms "nucleic acid molecule" and "sequence" are not used interchangeably herein. A "sequence" refers to the sequence information of a "nucleic acid molecule".

As used herein "mutable position" refers to the position of a nucleic acid that is susceptible to a given type of chemical mutagenesis.

As used herein "determining the number" refers to determining the lower bound number.

As used herein "X %" with respect to mutation rate, refers to the probability percentage of mutagenesis per mutable position of the multiple mutable positions that are present in a plurality of nucleic acid molecules. Thus, 25% mutation rate means a 25% probability of mutagenesis.

The terms "template", "nucleic acid", and "nucleic acid molecule", are used interchangeably herein, and each refers to a polymer of deoxyribonucleotides and/or ribonucleotides. "Nucleic acid" shall mean any nucleic acid, including, without limitation, DNA, RNA and hybrids thereof. The nucleic acid bases that form nucleic acid molecules can be the bases A, C, G, T and U, as well as derivatives thereof.

As used herein "contig" and "contiguous" refers to a set of overlapping sequence or sequence reads.

As used herein, the term "amplifying" refers to the process of synthesizing nucleic acid molecules that are complementary to one or both strands of a template nucleic acid. Amplifying a nucleic acid molecule typically includes denaturing the template nucleic acid, annealing primers to the template nucleic acid at a temperature that is below the melting temperatures of the primers, and enzymatically elongating from the primers to generate an amplification product. The denaturing, annealing and elongating steps each can be performed once. Generally, however, the denaturing, annealing and elongating steps are performed multiple times (e.g., polymerase chain reaction (PCR)) such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. The term "amplified nucleic acid molecule" refers to the nucleic acid sequences, which are produced from the amplifying process as defined herein.

As used herein, the term "bisulfite mutagenesis" refers to the mutagenesis of nucleic acid with a reagent used for the bisulfite conversion of cytosine to uracil. Examples of bisulfite conversion reagents include but are not limited to treatment with a bisulfite, a disulfite or a hydrogensulfite compound.

As used herein, the term "mapping" refers to identifying a location on a genome or cDNA library that has a sequence which is substantially identical to or substantially fully complementary. The nucleic acid molecule may be, but is not limited to the following: a segment of genomic material, a cDNA, a mRNA, or a segment of a cDNA.

As used herein, the term "methylation" refers to the covalent attachment of a methyl group at the C5-position of the nucleotide base cytosine. The term "methylation state" or refers to the presence or absence of 5-methyl-cytosine ("5-Me") at one or a plurality of CpG dinucleotides within a DNA sequence. A methylation site is a sequence of contiguous linked nucleotides that is recognized and methylated by a sequence specific methylase. A methylase is an enzyme that methylates (i. e., covalently attaches a methyl group) one or more nucleotides at a methylation site.

As used herein, the term "read" or "sequence read" refers to the nucleotide or base sequence information of a nucleic acid that has been generated by any sequencing method. A read therefore corresponds to the sequence information obtained from one strand of a nucleic acid fragment. For example, a DNA fragment where sequence has been generated from one strand in a single reaction will result in a single read. However, multiple reads for the same DNA strand can be generated where multiple copies of that DNA fragment exist in a sequencing project or where the strand has been sequenced multiple times. A read therefore corresponds to the purine or pyrimidine base calls or sequence determinations of a particular sequencing reaction.

As used herein, the terms "sequencing", "obtaining a sequence" or "obtaining sequences" refer to nucleotide sequence information that is sufficient to identify or characterize the nucleic acid molecule, and could be the full length or only partial sequence information for the nucleic acid molecule.

As used herein, the term "reference genome" refers to a genome of the same species as that being analyzed for which genome the sequence information is known.

As used herein, the term "region of the genome" refers to a continuous genomic sequence comprising multiple discrete locations.

As used herein, the term "sample tag" refers to a nucleic acid having a sequence no greater than 1000 nucleotides and no less than two that may be covalently attached to each member of a plurality of tagged nucleic acid molecules or tagged reagent molecules. A "sample tag" may comprise part of a "tag."

As used herein, the term "segments of genomic material" refers to the nucleic acid molecules resulting from fragmentation of genomic DNA.

As used herein, "substantially the same" sequences have at least about 80% sequence identity or complementarity, respectively, to a nucleotide sequence. Substantially the same sequences or may have at least about 95%, 96%, 97%, 98%, 99% or 100% sequence identity or complementarity, respectively.

As used herein, the term "substantially unique primers" refers to a plurality of primers, wherein each primer comprises a tag, and wherein at least 50% of the tags of the plurality of primers are unique. Preferably, the tags are at least 60%, 70%, 80%, 90%, or 100% unique tags.

As used herein, the term "substantially unique tags" refers to tags in a plurality of tags, wherein at least 50% of the tags of the plurality are unique to the plurality of tags. Preferably, substantially unique tags will be at least 60%, 70%, 80%, 90%, or 100% unique tags.

As used herein, the term "tag" refers to a nucleic acid having a sequence no greater than 1000 nucleotides and no less than two that may be covalently attached to a nucleic acid molecule or reagent molecule. A tag may comprise a part of an adaptor or a primer.

As used herein, a "tagged nucleic acid molecule" refers to a nucleic acid molecule which is covalently attached to a "tag."

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used herein, the term "wobble base pairing" with regard to two complementary nucleic acid sequences refers to the base pairing of G to uracil U rather than C, when one or both of the nucleic acid strands contains the ribonucleobase U.

As used herein, the term "substantially fully complementary" with regard to a sequence refers to the reverse complement of the sequence allowing for both Watson-Crick base pairing and wobble base pairing, whereby G pairs with either C or U, and A pairs with either U or T. A sequence may be substantially complementary to the entire length of another sequence, or it may be substantially complementary to a specified portion or length of another sequence. One of skill in the art will recognize that the U may be present in RNA, and that T may be present in DNA. Therefore, a U within an RNA sequence may pair with A or G in either an RNA sequence or a DNA sequence, while an A within either of a RNA or DNA sequence may pair with a U in a RNA sequence or T in a DNA sequence.

As used herein, a "wobble" primer is a set of primers where the sequence at mutable positions is equally likely to match the original base or the mutated base.

All publications and other references mentioned herein are incorporated by reference in their entirety, as if each individual publication or reference were specifically and individually indicated to be incorporated by reference. Publications and references cited herein are not admitted to be prior art.

This invention will be better understood by reference to the Experimental Details which follow, but those skilled in the art will readily appreciate that the specific experiments detailed are only illustrative of the invention as defined in the claims which follow thereafter.

EXPERIMENTAL DETAILS

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

Methods—Counting Templates (Single Read Length)

To enable a wide range of simulations, a library of Python programs was developed, (Example 11), to simulate mutation, sequencing, counting and assembly of distinct templates under the assumptions of error-free sequencing, perfect mapping, and uniformity of mutation sites, mutation rate, sequence coverage, and DNA amplification. Our ability to recover template count and assembly depends on the depth of read sampling, typically called "coverage". Coverage usually means the average number of reads overlapping a position in the reference genome, however herein, coverage means the average read depth over a position per template.

To measure template count over a single fixed read length for T templates, mutation was simulated to generate T random template patterns with R bits and a flip rate of p. To measure recovery under infinite coverage, the number of distinguishable mutation patterns observed was counted (Example code in Section Z). To measure recovery under finite coverage, reads were generated by sampling a fixed number of patterns with replacement from the pool before counting distinguishable patterns (Example code in Section Z). Amplification distortion could be modeled by altering the sampling procedure; however, results are restricted to the case of uniform sampling. Simulations explore mutation rates in the range of 0.05 to 0.35, template counts in the range of 2 to 1,024, and read lengths with 10, 20, and 30 mutable bits. For each condition, one hundred simulations were performed and record the average recovery under infinite coverage (FIG. 3, panel A). For each of those hundred simulations, one hundred finite samplings were performed for each coverage level of 1× to 5× per template and the mean count observed was recorded. Shown in FIG. 3, panel B are the results for the mutation rate of 0.35.

The first class of applications focuses on the general problem of determining absolute template count. This is important for determining the copy number of genomic DNA, measuring mRNA expression levels, quantifying allele bias, and detecting somatic mutations. To obtain an accurate count, the protocol requires mutagenesis prior to amplification. Amplification could be either short- or long-range PCR but must occur before fragmentation if needed for library preparation. The number of possible mutation patterns should exceed the template number to obtain the most accurate count. Hence, cases were only considered where the absolute template count is below the low thousands, and save the other cases for Discussion.

Example 1. Counting Templates (Single Read Length)

The simplest formulation is the case where the templates span a single fixed read length and exhaustive coverage (FIG. 3, panel A). In this case, the estimate of template count is merely the number of distinguishable mutation patterns observed.

The number of possible patterns depends on the number of bits per read, and the probability of observing a given pattern depends also on the flip rate. The optimal flip rate for generating distinct mutational patterns is 0.5, wherein every pattern is equally likely. However for a window of at least 20 bits, corresponding to a read length of 80 base pairs, a rate of 0.25 is still virtually perfect for template counts in the thousands. Similar efficacy is obtained at a flip rate of 0.15 for a 30-bit window. Templates numbering in the thousands are adequate for genome copy number determination or single-cell transcript profiling. In Section Z, example code is provided to simulate performance under a variety of conditions.

The recovery of template count was also demonstrated subject to varying depth of coverage for a fixed flip rate of 0.35 (FIG. 3, panel B). For each simulation, T initial template molecules were mutated, creating a pool of patterns. At a coverage level of c, c×T patterns were selected with replacement from the pool and record the number of distinct patterns. For high coverage, on the order of 4× per original template molecule, recovery of count is nearly perfect. At lower coverage the count is underestimated, the inevitable consequence of undersampling. These simulations assume uniform PCR amplification and provide an upper bound on performance.

Methods—Counting Templates (Multiple Read Lengths)

When the template length exceeds a single window, a few simple graph formalisms are used. Two reads are said to "conflict" if they map to overlapping positions and their overlaps fail to agree. A "compatible read graph" was defined to be one in which each distinguishable read is treated as a "vertex" and two vertices are "compatible" and connected by an "edge" if the reads could have originated from the same template. In the case of finite coverage, two reads are compatible if they do not conflict. In the case of infinite coverage, there is a stronger constraint: two reads at a distance d mutable bits apart are compatible if all d−1 were observed to be distinct, non-conflicting, intermediate reads (Example code in Section Z). All edges inherit a direction from the orientation of the reference template such that each vertex has in-edges extending from one end of the template and out-edges extending toward the other end.

A path in this graph represents a possible partial assembly of an initial template pattern. Consequently, determining the minimum number of templates needed to explain all of the reads is achieved by finding the minimum number of paths such that every vertex in the graph is included in at least one path. This is known as the minimum vertex cover and in general is an nondeterministic polynomial time hard (NP-hard) problem. However, under the assumption of perfect read mapping to a linear genome, our graph is not only directed, but also acyclic. By Dilworth's theorem the minimum number of covering paths is equivalent to the maximum number of elements in an antichain (Dilworth, 1950). In other words, the minimum number of templates needed to explain the reads is equal to the maximum number of reads that are pairwise incompatible. Using König's theorem König, 1931), this problem was solved by finding a maximal matching in a new bipartite graph constructed by splitting each vertex in two (an "in" vertex that receives in-edges and an "out" vertex that receives out-edges). Finding a maximal matching in a bipartite graph is then solvable in polynomial time by the Hoperoft-Karp algorithm (Hoperoft and Karp, 1973).

As in the case of a fixed read length, mutation was simulated to generate a pool of template patterns. For a finite coverage level of c, read length R, and T initial templates of length L, c×T×(L/R) reads were generated by drawing uniformly with replacement from the set of templates and read start positions. These reads were used to build a compatible read graph, convert to a bipartite graph, and apply Hoperoft-Karp to find a maximal matching.

In the case of finite coverage, all reads that do not overlap are by definition compatible. This implies that the maximal antichain (comprised of reads that are all pairwise incompatible) must be comprised of reads all in which all overlap and therefore all start within a single interval of length R. This fact permits a significant computational simplification: instead of computing the maximal antichain for the entire graph, smaller subgraphs of reads can be restricted whose start positions are contained in the interval [nR, (n+2)R] for n=0, . . . , (L/R)−1; identify a maximal antichain over each interval; and compute the maximum size over all intervals (Example code in Section Z). For a fixed mutation rate of 0.35, emplate counts were simulated in the range of 2 to 1,024, reads of 10, 20, and 30 bits, templates that are 16 read lengths long, and a coverage of 1× to 5×. For each condition, 100 simulations were performed and the mean number of templates recovered were reported.

Example 2. Counting Templates (Multiple Read Lengths)

More often, the length of the template will exceed a single read length. In this case, there was no fixed window over which to count distinct mutational patterns. So instead of looking for the number of unique (and hence incompatible) patterns over a fixed window, a maximal set of pairwise incompatible reads was determined. This problem can be precisely stated in the language of graph theory. More specifically, reads were treated as vertices, and connected by directed "compatible" edges whenever two reads can derive from the same template. The direction of the edge is determined by the orientation of the reference template. The result is a directed acyclic graph. By Dilworth's theorem (Dilworth, 1950), the size of the largest set of pairwise incompatible reads is the same as the minimum number of paths covering all vertices of this graph. By König's theorem (König, 1931) this is a problem of maximal matching in a bipartite graph, which is computationally tractable and solvable in polynomial time with the Hoperoft-Karp algorithm (Hoperoft and Karp, 1973). In FIG. 3 panel C, the results are shown for a fixed mutation rate of 0.35, a template that spans 16 read lengths, for depths of coverage ranging from 1× to 5× per template, and for template counts ranging from 2 to 1,024. Under similar conditions of flip rate and coverage, counting over long templates is comparable to performance in counting over a fixed window, as described above.

The simulations of this section provide guidelines for (i) genome wide copy number determination, (ii) transcript profiling, and (iii) determining allelic ratios. To determine copy number, the ratio of count was measured for a given locus to the median count over the remainder of the genome. For transcript profiling, the proportionate counts of each gene transcript were measured. To determine allelic imbalance, the ratio of counts was measured from templates distinguishable by at least one SNV. In the context of RNA, this also enables observation of biased allele expression resulting from chromosome inactivation, imprinting and the like.

Methods—Assembling Templates

In the counting problem, a conservative estimate was established for the initial number of templates by allowing all compatible edges between reads. For the assembly problem, however, high probability assemblies were to be established. Consequently, the compatible edge graph was restricted to a sub-graph composed of the best edges. When coverage is exhaustive, a very precise definition of best edges can be formulated. Two R-bit reads were joined by an edge if they overlap and agree for R−1 bits. Consequently, two tags of a template are exactly matched if and only if every such R−1 bit string across its span has a unique pattern. When the condition is not met—for example due to too many templates and/or too few flipped bits—connected end tags that were not exactly matched were found (Example code in Section Z).

When coverage is finitely sampled, there are many ways to select the best edges for a subgraph (FIG. 5). A simple scoring method was applied that assigns a weight to an edge that reflects how unlikely it is that the reads agree on their mutation patterns by chance. Given two reads that overlap and agree on a window of size M with K bits flipped, the edge was weighted by $-\log(p^K(1-p)^{M-K})$ where p is the flip rate. All of the edges in order of decreasing weight were iterated through. An edge e from A to B is selected for inclusion in the subgraph if no edge from A or to B has already been selected that has a weight strictly greater than e. This procedure was carried out for each simulation and extract from the resultant subgraph all exact matches. Unlike the case for exhaustive coverage, exact matches may be incorrect. Because this is a simulation, the truth was known and the number of exact matches that are correct and incorrect was recorded. Whether the exact path is also true was also recorded (Example code in Section Z).

Example 3. Assembling Templates

The second class of applications is to correctly assemble reads by their mutation patterns in order to recover the proper end-to-end sequence of nearly identical templates, desired when determining haplotype phasing or enumerating transcript isoforms. Long templates each tagged uniquely at both ends were considered to simulate the more general task of determining how many initial templates can be correctly assembled from end to end from the mutation pattern alone (FIG. 2).

Following mutagenesis, amplification, fragmentation, and sequencing, reads were connected with overlapping mutation signatures to assemble a path from one tag to the other. Whereas in the previous application, all compatible edges between reads were allowed, for this problem a subgraph was built with only the "best edges" between overlapping reads. A pair of tags is "exactly matched" if there is a path in the subgraph that connects them and neither tag is connected to another tag. Such a path is called an "exact path." If two tags originate from the same template, they are a "true match." A "true path" is an exact path for which every read originates from the same initial template.

Determining performance for the general task provides a lower bound on performance for other applications, because if there is an exact path that is also true, then all sequence information for that template was correctly observed. This includes haplotype phasing in the case of genomic data and transcript structure in the case of RNA profiling. In fact, these two applications are less demanding than the general task because there will only be a few template varieties and each template variety provides additional sequence information for distinguishing them.

The case of exhaustive coverage was considered to establish the best performance that can expect for a given set of conditions. In this case, the best edges are naturally defined as the set of compatible edges that overlap for all but one bit. In FIG. 4 panel A, the effect of flip rate on template assembly was explored. At a flip rate of 0.35 and 30 bits per read, performance on 32 template molecules is nearly perfect for even the longest span tested, $2^{10}$ read lengths, in excess of 100 kilobases.

With exhaustive coverage, best edges are unambiguously defined and have the property that exactly matched pairs and exact paths are also true. However, for finite coverage, there is no natural definition of best edges and exactly matched pairs and exact paths may not be true. For finite coverage, weights to edges were assigned by likelihood and a greedy algorithm was used to select the best subgraph (detailed above and illustrated in FIG. 5).

FIG. 4 panel B explores the effect of coverage (2× to 14× per template) on recovery of exact matches as a function of template length (2 to 1,024 read lengths), for 32 templates, a 30 bit read length, and a flip rate of 0.35.

In FIG. 4 panel C, the template length was fixed to 32 read lengths to show recovery as a function of the number of templates, from 2 to 1,024 under the same conditions. Because these are simulations and the ground truth was known, the proportion of exact matches are true and false can be determined, and these numbers shown. All exact matches are connected by an exact path, and for the conditions explored here, virtually all true exact matches are connected by a true path. At the maximum level of coverage, nearly all the true paths were determined, even for spans of $2^{10}$ read lengths. For haplotype phasing, it is sufficient to have a single true path, and this is attainable with high probability at a lower coverage, 10× per template.

Methods—Partial Bisulfite Mutagenesis

Partial bisulfite mutagenesis was obtained in a single stranded phi x 174 genomic DNA using the MethylEase™ Xceed Rapid DNA Bisulphite Modification Kit (Human Genetic Signatures). The full conversion protocol was modified by changing the incubation temperature to 73 degrees Celsius (from 80 degrees Celsius) and the incubation time to 10 minutes (instead of 45 minutes). Four regions were amplified to measure the conversion rate.

Using the MethylEase™ Xceed Rapid DNA Bisulphite Modification Kit (Human Genetic Signatures), the default incubation temperature (default 80 degrees Celsius) and time (default 45 minutes) were modified. A range of temperatures were tested (65, 73 and 80 degrees Celsius) and a range of times were tested (0, 3, 10, 30, 45 minutes). The remainder of the protocol remains the same.

After bisulfite treatment, four specific regions of phi x were amplified with "wobble" primers which contain a mixture of oligonucleotides such that the mutable positions are guanine (G) or adenine (A) for the forward primers and cytosine (C) or thymine (T) on the reverse primers. The addition of A-tails and ligation of Illumina sequencing adapters and sequence resulted in a sequence which was mapped back to the phi x genome using a simple dictionary mapping method using a fully converted genome and fully converting all reads before mapping.

The best results (60% conversion) were obtained at an incubation of 10 minutes at 73 degrees. A conversion rate of 20% was also obtained by incubating for 3 minutes at 73 degrees.

Methods—Custom Sequencing Primers

```
SEQ ID NO: 1:
ACACTCTTTCCCTACACGACGCTCTTCCGATC*T
```

The sequencing primer (Seq ID p5.mC), wherein the cytosines (C) are methylated, and wherein *T is a phosphorothioated thymine to protect the ends from degradation by exonuclease.

```
SEQ ID NO.: 2:
/5Phos/GATCGGAAGAGCGGTTCAGCAGGAATGCCGA*G
```

The sequencing primer (SEQ ID NO:2), wherein the cytosines (C) are methylated, wherein *G is a phosphorothioated guanine to protect the ends from degradation by exonuclease, and wherein 5Phos is a 5'-phosphorylated, deoxyuridine-containing anchor-primer.

Example 4. Partial Bisulfite Mutagenesis

The experimental results from partial bisulfite mutagenesis of a phix template genome (FIG. 6). The full conversion protocol was modified by changing the incubation temperature to 73 degree Celsius (from 80 degrees Celsius) and the incubation time to 10 minutes (instead of 45 minutes). Four regions were amplified to measure the conversion rate.

FIG. 6 panel A depicts the rate at which each base is observed over all the data for those positions with a coverage of at least 30 reads. Nearly all the C positions are at 40% C and 60% T. For each of the four regions amplified, conversion patterns were compared between reads. Not all regions are equally well covered in the data, with 40-4500 reads. FIG. 6 panel B depicts the cumulative distribution of the conversion rate per read. FIG. 6 panel C depicts correlation in flips for all cytosines in the targeted region. It was determined that there none. FIG. 6 panel D depicts the data of FIG. 6 panel C as a histogram.

For the best amplified position, it is clear that partial conversion was determined with a 60% flip rate randomly distributed throughout each read.

Discussion—Examples 1-4

Presently, inferring the long-range structure of the DNA templates is limited by short read length. Accurate template counts suffer from distortions occurring during polymerase chain reaction (PCR) amplification. The utility of introducing random mutations in identical or nearly identical templates was explored to create distinguishable patterns that are inherited during subsequent copying. Simulations of the applications of this process were performed under assumptions of error free sequencing and perfect mapping, employing cytosine deamination as a model for mutation. The simulations demonstrate that within readily achievable conditions of nucleotide conversion and sequence coverage, accurately counting the number of otherwise identical molecules as well as connecting variants separated by long spans of identical sequence can be achieved. Many potential applications include, transcript profiling, isoform assembly, haplotype phasing, RNA expression analysis, copy number determination and de novo genome assembly.

Counting varietal tags can be used to mitigate the effects of amplification bias. While the original message is completely recoverable, the tag is confined to one end of the molecule such that identity and count can only be distinguished within one read length of the ends. Only reads that include the tag are useful in determining count and varietal tags provide no solution for assembly and assortment.

There are also protocols designed to aid sequence assembly of regions that are resistant due to base composition or repeat structure, which rely on misincorporation of artificial nucleotides during amplification (Keith et al., 2004a; Keith et al., 2004b; Mitchelson, 2011). Implementation of this method requires many steps, and is not amenable to high throughput process, and in addition to such technical hurdles, is not suitable for counting as it loses track of template count.

Figure 1:
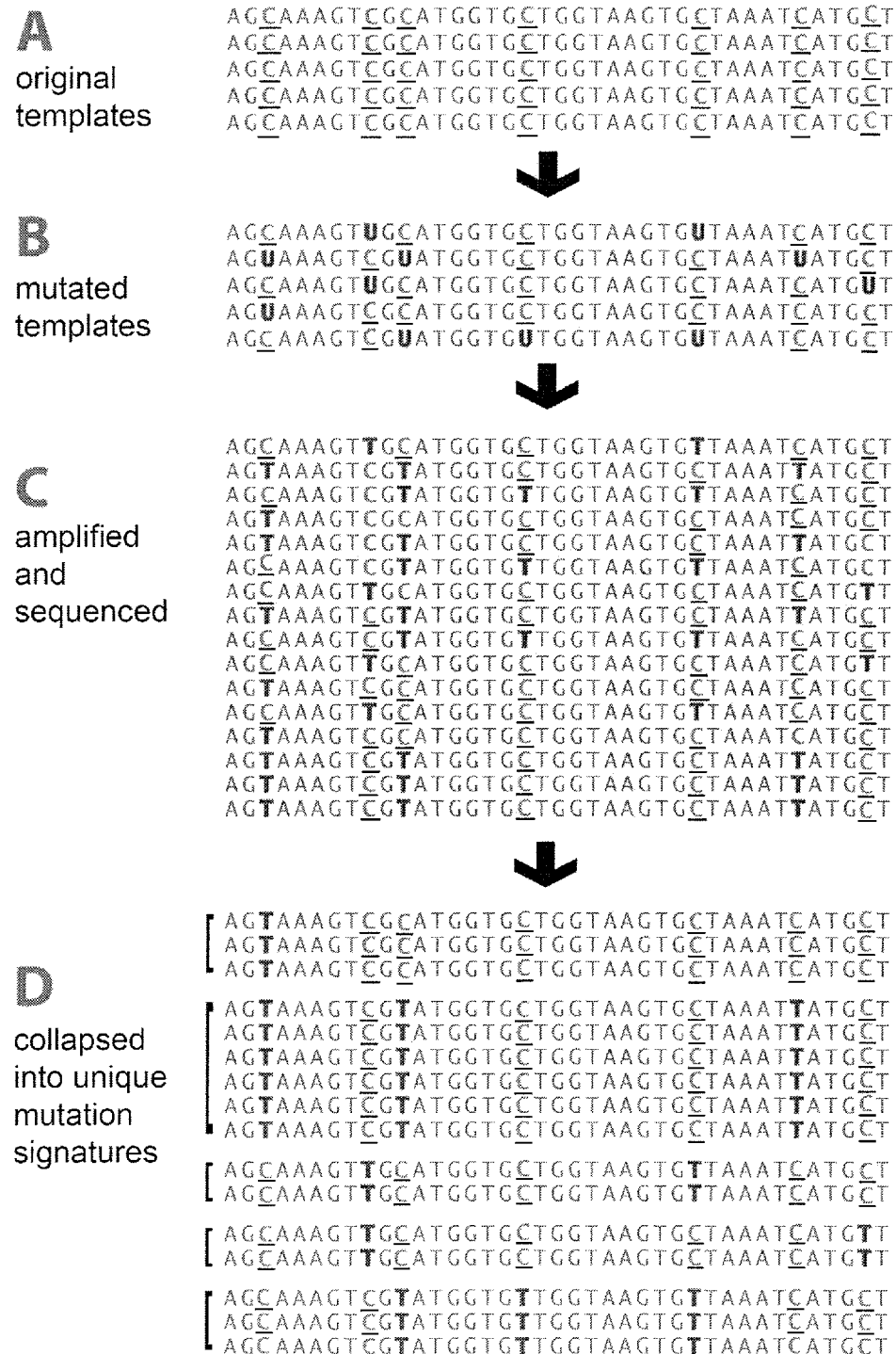
FIG. 1. Enumerating Templates Over A Fixed Window

Described herein are different approaches for counting and assembling templates using template mutagenesis. The non-limiting examples herein demonstrate by simulation that template mutagenesis can solve both the problems of counting and assembly. For any application, the order of operation is mutagenesis first, followed by short- or long-range PCR, then fragmentation, if needed, and preparation of sequence libraries. Two classes of applications were explored. The first is counting specific DNA or RNA molecules, for assessing genome copy number or profiling a transcriptome (FIG. 1). The second is sequence assembly—for example establishing haplotypes or distinguishing transcript isoforms (FIG. 2).

The simulations model partial bisulfite mutagenesis of single stranded DNA (Shortle and Botstein, 1983): each mutable position (or "bit") converts (or "flips") independently from a wild-type state to an altered state with a fixed probability (or "flip rate"). Performance was simulated under a variety of reasonable parameters for read length and mutation rate, and over a range of template lengths and counts. The results are presented under an assumption of complete coverage to obtain a theoretical upper limit of performance and then consider the consequences of sampling to various levels of coverage. In the simulations, mutable positions are distributed uniformly throughout the template such that each read contains the same number of bits (or "bit length"). Sequence or mapping error are not presently incorporated. Variations to these assumptions and procedures are addressed herein.

A feasibility study and guide is presented for template mutagenesis as an enhancement to sequence based analysis. Such methods introduce random mutations to create distinguishable patterns in previously identical or nearly identical templates. These patterns are inherited in copies of the template, and portions of patterns remain in fragmented copies. Provided these fragments overlap and there is sufficient diversity in mutational patterns over a read length, the structure of each original template can be inferred, thus overcoming the loss of connectivity resulting from short read lengths. The accuracy of template counting also improves, undistorted by biased amplification. The applications of this process were simulated under assumptions of error-free sequencing, perfect mapping, uniformly distributed reads, and uniform bit distribution. The simulations suggest that within readily achievable conditions accurately counting the number of otherwise identical molecules can be determined, as well as connecting variants separated by long spans of identical sequence. There are many potential applications, ranging from transcription profiling and isoform assembly to haplotype phasing and de novo genome assembly.

To illustrate one application of the results, characterizing single cell gene expression was considered. A mammalian cell has ~350,000 mRNA transcripts with an average length of 1,500 nucleotides (Alberts, 1994). Single strand cDNA would be randomly mutagenized using cytidine deamination before amplification, fragmenting, and sequencing. Assuming uniformity of sequence coverage and uniformity of PCR amplification, 9 million 100 base pair paired-end reads yields an average of 4× coverage per template. Given the typical distribution of cytidine in mammalian genomes, 30 is a reasonable estimate for the number of mutable positions in a read pair. From FIG. 3 panel C, it is clear that RNA templates can be counted with near perfect accuracy for mRNA species of intermediate to scarce expression (<1,000 copies per cell).

Furthermore, many mammalian genes are alternatively spliced, resulting in a diversity of isoforms observable as different patterns of exon inclusion in the mRNA. At a read depth of 10× per template, or 23 million reads, count can be determined not only transcripts per gene, but also expression at the level of individual isoforms: Even without the additional information gained by observing alternative splice junctions, a true path can be assembled from one end of the molecule to the other. This can be accomplished for all but the most abundant genes and very long transcripts (greater than 6,000 nucleotides; FIG. 4, panel C). In contrast, varietal tagging can achieve accurate counting of gene transcripts, even long and abundant ones, but it is limited to labeling the end of a molecule and so does not allow counting of isoforms or observing sequence variants, except near the ends of transcripts. The two methods, varietal tagging and mutagenesis can be seamlessly integrated, achieving the benefits of both methods.

Another direct application of template mutation is discriminating haplotypes in an individual. Using existing short-read technology, many of the heterozygous positions can be readily identified; however, because the polymorphisms are typically more than one read length apart, the proper phasing of alleles cannot be determined. The following procedure for phase recovery is proposed: first perform partial deamination on high-molecular-weight DNA with a 0.35 flip rate, then dilute it to 30 initial templates per region for each of the two strands. Then amplifying with randomly primed PCR, and fragmenting as needed for preparing sequencing libraries. Under the assumption of uniformly distributed coverage (FIG. 4 panel B), it is observed that coverage of 10× per initial template would be sufficient to recover phase information for variants separated by hundreds of kilobases.

Further, the ability to establish phase by this method depends on strong concordance between the haplotypes and the reference genome. For those regions where the reference genome is a poor match, due to repeat content, large-scale rearrangements or novel sequence, the mutation pattern assembly algorithm will fail to generate consistent end-to-end assemblages. Although this presents a problem for direct inference by reference-matched phasing, it provides an opportunity for de novo haplotype assembly. The SUTTA algorithm (Narzisi and Mishra, 2011) assembles haplotypes from short-read data by scoring proposed local assemblies based on orthogonal data sources, such as coverage, mate pairs, or physical maps. Template mutagenesis can help. Each local reference genome that SUTTA considers can also be assigned a score based on the number of successful end-to-end mutation pattern assemblies over the region. The result would be a de novo assembly over the human genome for those difficult regions.

In the simulations, focus is on a specific form of mutation: the conversion of cytidine to uridine by deamination. This conversion can be achieved either chemically through bisulfite treatment (Shortle and Botstein, 1983) or enzymatically through activation-induced deaminase (Bransteitter et al, 2003). The advantages of deamination are that conversion patterns are predictable. Moreover, because bisulfite treatment is widely used in DNA methylation assays, the computational tools for mapping deaminated sequence reads are readily available. Still, other methods of mutagenesis, such as depurination, transposition, alkylating agents, or inducing replication error in the first template copy might be useful in some contexts.

In the simulations perfect mapping was assumed. In practice, however, the ability to map reads might be somewhat degraded by template mutation. For a deamination protocol, a standard practice is to map to a reduced alphabet where all cytosines ("C"s) are converted to thymines ("T"s) in both the read and the reference, with two distinct references genomes for each DNA strand (Krueger et al., 2011; Otto et al., 2012). Clearly, restricting to a smaller alphabet and doubling the reference genomes impacts the ability to unambiguously map reads, however, the effect is surprisingly mild (Krueger et al., 2012). If increased mapping efficiency is needed, the mapping algorithm can be augmented with a probabilistic model of the flip rate to prioritize the most likely alignments.

In the simulations no sequence error was assumed, but methods will be necessary for handling these. Aside from its effects on mapping, sequence error may reduce the ability to recover mutation patterns in those cases where the error appears to flip a bit or reverse a flipped bit. Fortunately, sequence error is typically rare. Within a reasonable range for flip rate, window size, and template count, sparse mutational patterns are expected, well separated so that no two patterns are very much alike. Sequence error will produce a pattern "nearby" an established pattern, and less well covered, and this signature can be used to discount those reads.

The simulations demonstrate that most applications work best for a low initial template count, less than a few thousand. This is not a problem for many genomic applications and is close to ideal for single-cell RNA analysis. If analysis of greater numbers of template molecules is desired, for example during analysis of bulk mRNA, then after mutagenesis of the first strand cDNA, multiple separate amplifications reactions can be performed, each with low template count. The products of each reaction can be tagged with barcodes, pooled and sequenced.

Example 5. Assembling Templates

A mutational protocol, muSeq, was established for partial bisulfite conversion. The description of the method is very similar to that established for the phiX samples discussed above. To establish the operating characteristics of the protocol, a study was performed on a PstI digest of a human genome.

The experiment is described here. Genomic DNA is digested with a restriction enzyme (PstI). Fragments are end-repaired, adenylated, and then ligated to bisulfite resistant sequencing adapters. These adapters match the standard Illumina adapters, save that the cytosines are replaced by methyl-cytosines. The sample is then treated with a standard kit for bisulfite treatment (MethylEasy Xceed Rapid DNA Bisulphite Modification Kit Mix; Human Genetic Signatures.) Instead of incubating the sample for the standard of 80° C. for 45 minutes, 3, 6, and 9 minutes at 73° C. were tested. One library using the standard 80° C. and 45 minutes was also generated. The samples were sub-sampled, amplified and sequenced.

The resulting reads were mapped to the genome using an informatics pipeline designed for bisulfite sequence data. First the read-pairs are fully converted. For read 1, every C is converted to a T and for read 2, every G to an A. The converted read-pairs are then mapped twice, once to a genome where every C is converted to a T and once to a genome where every G is converted to A. The best mapping was assigned to the original read-pair and the mapped genome recorded. Reads that map to the AGT-genome are called "original top" or "OT" and are templates derived from the top strand of the initial restriction fragment. Similarly, the reads that map to the ACT genome are called "original bottom" or "OB." Focus was on a 135 thousand fragments with high quality alignments in the range of 150 to 400 base pairs.

The first observation, demonstrated in FIG. 7, is that the same mutational rate can be reliably established by setting the incubation time. Also the mutational rates fall within the desired range.

Each restriction fragment/strand provides an opportunity to observe multiple reads derived from the same initial template. In error-free data, one need only cluster reads that have precisely the same pattern. However, because of errors in sequencing and PCR amplification, a robust method was developed for joining reads derived from the same initial template. Information was extracted from all convertible positions and then cluster reads using a multi-scale clustering algorithm that works on pair-wise hamming distances [arXiv:1506.03072 (clustering method devised is available at arvix.org/abs/1506.03072)]. An example of clustered reads at a single restriction fragment for the original top strand is shown in FIG. 8.

To more carefully study the properties of the mutational sequencing, we sequenced the 6 minute conversion sample at great depth, on two lanes of a nextSeq. When cytosine (or bit) positions were examined, the mutations were found to be uncorrelated. Selecting 100,000 random pairs of bits, we compute the Fisher exact test and compare to the theoretical expectation that the two sites are independent. The resulting Q-Q plot is linear suggesting that the observed distribution does not diverge from the null expectation and that deamination events are random and independent (FIG. 9).

The conditions of digestion, amplification, and sequencing imply that the mean that coverage is not uniform for each locus. However, on the whole, the counts of template from the autosome and the X chromosome differ at a ratio of two to one, as expected in our male sample (FIG. 10).

To study copy number in the context of identical sequence and coverage bias, we examine positions in the sample that are heterozygous. Heterozygous loci are nearly identical for sequence and so suffer the same distortions. When the observed distribution was computed using template count, alleles were found to conform to the expected binomial distribution (FIG. 11). The fit is far less good when the reads were used instead of the template counts (FIG. 12). This suggests that template count is superior for comparing copy number against a known difference. For example, counting the relative proportion of a rare SNP or determining copy number in the presence of a reference.

Finally, collapsing reads with the same pattern were found to reduce the error in each template. By examining reads from homozygous positions, 99.92% of consensus read positions were found to have greater than 80% of base pairs showing the homozygous base. This reduces typically sequencing error rates by 100-fold.

Conversion of cDNA

The mutational protocol can be applied to cDNA as well. While this data is less well-studied, the preliminary results are very promising. Taking whole RNA derived from cell lines, the mRNA was reverse transcribed with poly-T and template switch oligo primers that are resistant to bisulfite mutation (methyl-cytosines substituted for cytosines). The resulting first strand cDNA were mutagenized with the muSeq protocol for 6 minutes at 73 C. The mutated strands were then sub-sampled, amplified, sonicated, repaired, and ligated to sequencing adapters, amplified and sequenced.

The resulting reads were then converted two ways (read 1 C→T, read 2 G→A; and read 1 G→A, read 2 C→T) mapped to two versions of the human genome using the STAR mapper (Dobin, et al STAR: ultrafast universal RNA-seq aligner, Bioinformatics. 2012) much as described above. The best of the four maps were selected to assign to the original read.

Plots showing stacks of reads in the IGV viewer are shown in FIGS. 13 and 14.

Preliminary results were obtained suggesting that long transcript structures can be recovered without mapping the reads at all but relying instead on methods of de novo assembly.

Example 6. Error Reduction

Using the high-coverage data with the 6 minute incubation and 5 rounds of post-bisulfite linear amplification, the properties of the consensus sequences derived by clustering reads with the same mutation pattern were examined. Only genomic positions that are not bits and are confidently homozygous in our sample were considered. For each consensus sequence base, the proportion of reads reporting the homozygous base (homozygous base fraction) was determined. Greater than 99.99% of consensus bases have a majority of reads in agreement with the homozygous base. Under more stringent requirements, it was found that 99.92% of consensus bases match the homozygous base for greater than 80% of reads in the template (FIG. 13). These values bound the error rate as some of the disagreement is likely due to true somatic mutation. Nevertheless, these error rates are orders of magnitude below sequencer error, which is commonly observed at about one base error per position per read.

Methodological Improvements

1. Direct mutagenesis of RNA. The RNA sequence can be directly mutagenized before reverse transcription.
2. Mutagenesis on beads or surfaces. By binding template molecules to a bead or surface, for instance by attaching biotinylated primers to the templates and binding with streptavadin beads, yield of post mutation templates may be improved. Also multiple independent amplifications from the bound targets to circumvent PCR error may be performed.
3. Binding to linear products of mutagenized templates to beads. Similar to 2.

Example 7. Detecting One or More Variants

Example 7A—Detecting Tumor Cells

A sample is obtained from a subject afflicted with cancer. The sample is subjected to a chemical mutagenesis as described herein. The mutagenized sample is sequenced, aligned, mapped, and counted as described herein.

The presence of tumor cells in the sample is determined. Also, quantification of tumor cells in the sample is determined. Also, one or more rare mutations in the sample is determined. Also, one or more single nucleotide polymorphisms in the sample is determined. Also, benign and malignantly transformed cells is distinguished.

Example 7B—Detecting a Small Load of Cancer DNA in the Presence of an Excess of Normal DNA A sample is obtained from a subject afflicted with cancer. The sample is subjected to a chemical mutagenesis as described herein. The sample is further subjected to beads and/or varietal tags. The mutagenized sample is sequenced, aligned, mapped, and counted as described herein.

The presence of tumor cells in the sample is determined. Also, quantification of tumor cells in the sample is determined. Also, one or more rare mutations in the sample is determined. Also, one or more single nucleotide polymorphisms in the sample is determined. Also, benign and malignantly transformed cells is distinguished.

Example 7C—Detecting Prenatal Abnormalities

A sample is obtained from a pregnant female. The sample is subjected to a chemical mutagenesis as described herein. The mutagenized sample is sequenced, aligned, mapped, and counted as described herein.

One or more rare mutations in a fetus is determined. Also, one or more single nucleotide polymorphisms in a fetus is determined. Also, one or more chromosomal abnormalities in a fetus is determined.

Example 8. Sensitive Detection of Mutations

The error reduction described above in Example 6 is used in conjunction with the beads and/or varietal tags to obtain sequence counts for rare variants.

Example 9. De Novo Transcriptome Assembly

A group of RNA transcripts in one cell or a population of cells is obtained. The group of RNA transcripts is subjected to a chemical mutagenesis and sequenced as described herein.

An assembly algorithm is applied to the sequences of the group of RNA transcripts. In some embodiments, the assembly algorithm may be SOAPdenovo-Trans, Velvet/Oases, Trans-ABySS, or Trinity transcriptome assemblers. A transcriptome is obtained without mapping to a reference genome.

Example 10. Metagenomics

A group of NAMs is obtained from genomes from a large variety of organisms, wherein some of the organisms may be highly related. The group of NAMs is subjected to a chemical mutagenesis and fragmentation as described herein.

The group of mutagenized fragments of NAMs is sequenced. In some embodiments, the sequencing may be metagenome sequencing, shotgun sequencing, or high-throughput sequencing.

An assembly algorithm is applied to the sequences of the group of mutagenized fragments of NAMs. In some embodiments, the assembly algorithm may be Phrap, Celera, or Velvet/Oases assemblers. Independent genomes are assembled.

Example 11. Python Programs Developed for a Wide Range of Simulations

```
fixed_window_finite_coverage
'''
Performs simulations testing the recovery of template count
over a fixed window for a range of flip_rates, read_lengths,
and template_counts
assuming finite coverage
'''
import sys
import numpy as np
from support_functions import getRandomPatterns, toBinary, tabprint
fixes a random seed
seed=hash("This is not a random seed.")
np.random.seed(seed)
input parameters
numsim=100 ## template simulations
covsim=100 ## sampling reads
read_lengths=[10, 20, 30]
flip_rates=np.linspace(0, 0.35, 8)[1:]
template_counts=2**np.arange(1,11)
coverages=np.arange(1,17)
headings=['R', 'p', 'T', 'coverage', 'mean distinct']
print "\t".join(headings)
for each read length, flip rate and number of templates
for read_length in read lengths:
    for flip_rate in flip rates:
        for template_count in template counts:
            ## perform numsim sims
            unique_counts=[list( ) for_in range(len(coverages))]
        ## for storing results
        for sim in range(numsim):
            ## generate template patterns and convert to binary
               representation as int
            templates=getRandomPatterns(template_count, read_length, flip_rate)
            templates_binary=np.array([toBinary(x) for x in templates])
            ## for each level of coverage
            for ind, coverage in enumerate(coverages):
                num_reads=coverage*template_count
                ## csim times
                for csim in range(numsim):
                    ## sample uniformly from the templates
                    read_template=np.random.randint(0, template_count, num_reads)
                    ## consider just the observed templates
                    templates_observed=np.unique(read_template)
                    ## and ask how many are unique, saving the result
                    unique_count=len(np.unique(templates binary[templates observed]))
                    unique_counts[ind].append(unique_count)
        ## after the sims are done
        for ind, coverage in enumerate(coverages):
            ## compute mean for each coverage level and print
            mean_unique=np.mean(unique_counts[ind])
            info=[read_length, flip_rate, template_count, coverage, mean_unique]
            print tabprint(info)
            sys.stdout.flush( )
fixed window finite coverage
'''
Performs simulations testing the recovery of template count
over a fixed window for a range of flip rates, read_lengths,
and template_counts
assuming exhaustive coverage
'''
import sys
import numpy as np
from support_functions import getRandomPatterns, toBinary, tabprint
fixes a random seed
seed=hash("This is not a random seed.")
np.random.seed(seed)
input parameters
numsim=100
read_lengths=[10, 20, 30]
flip_rates=np.linspace(0, 0.5, 11)[1:]
template_counts=2**np.arange(1,11)
headings=['p', 'T', 'mean_distinct']
print "\t".join(headings)
all_data=[ ]
all_info=[ ]
for each read length, flip rate and number of templates
for read_length in read_lengths:
    for flip_rate in flip_rates:
        for template_count in template_counts:
            unique_counts=[ ]
            ## perform num sim simulations
            for sim in range(numsim):
                ## generate template patterns and convert to binary
                   representation as int
                templates=getRandomPatterns(template_count, read_length, flip_rate)
                templates binary=np.array([toBinary(x) for x in templates])
                ## count how many are unique and save answer
                unique_count=len(np.unique(templates_binary))
                unique_counts.append(unique_count)
            ## compute mean of sims and output results
            mean_unique=np.mean(unique_counts)
            info=[read_length, flip_rate, template_count, mean_unique]
            all_info.append((read_length, int(100*flip_rate), template_count))
            all_data.append(unique_counts)
            print tabprint(info)
            sys.stdout.flush( )
``` many_windows_finite_coverage_assembly
'''
Performs simulations testing the recovery of template
assembly over a template of many read lengths for a fixed
flip_rate,
and a range of read_lengths, and template_counts,
and the number read lengths in the template
and a range of template coverage.
Scores edges based on likelihood of accidental agreement
and starting with the most unlikely edges,
adds a new edge if neither vertex already has a partner
in that direction with a better score.
Allows multiple edges when scores exactly agree
and so acts like the infinite case in the limit of total coverage.
'''
import numpy as np
import sys
import time
from support_functions import getRandomPatterns, getMatch, \
    getWordSpace, getOneCount, getScoreTable, \
    greedyAssembly, pathScore, tabprint
from collections import defaultdict
input parameters
read_length=30
seed=hash("This is not a random seed.")
flip_rate=0.35
span_lengths=(2**np.arange(5,6))*read length
template_counts=2**np.arange(1,11)
coverages=2*np.arange(1,9)
fixes a random seed
np.random.seed(seed)
headings=["template length", "span length", "read length",
    "flip rate", "template count", "coverage",
    "true exact match", "false exact match", "true path",
    "false path", "time"]
print "\t".join(headings)
for each read length, flip rate and number of templates
for span_length in span_lengths:
    for template_count in template_counts:
        ## we generate a template with a read length on either side
            of the span
        template_length=2*read length+span_length ## length of
            template
        left_edge=read_length ## left edge of span (first read
            position to not contain left mark)
        right_edge=span_length ## right edge of span (last read
            position to not contain right mark)
        ## generate template patterns
        templates=getRandomPatterns(template_count, template
            length, flip rate)
        ## make unique matched markers at the ends of the span
        Apos_marks=np.arange(template_count)
        Bpos_marks=np.arange(template_count)
        Apos=read_length−1
        Bpos=read_length+span length
        marks={Apos:Apos_marks, Bpos:Bpos_marks}
        ## compute matches between templates over all possible
            windows
        match=getMatch(templates, read_length, marks=marks)
        ## find space of unique reads
        word_space=getWordSpace(match)
        ## get count of ones, for every template, position, and
            window size
        one_count=getOneCount(templates, read_length)
        ## get score lookup table
        score_table=getScoreTable(read_length, flip_rate)
        ## maximum read start position contained in the template
        max_start=template_length−read_length+1
        for ind, coverage in enumerate(coverages):
            t0=time.time( )
            num_reads=int(coverage*template_count*(float(template_length)/float(read_length)))
            ## generate reads
            read_template=np.random.randint(0, template_count,
                num_reads)
            read_start=np.random.randint(0, max_start, numreads)
            ## re-index reads from template space to word space
            ## word space assigns ambiguous reads to their least
                template
            read_index=[word_space[x] for x in zip(read_template,
                read_start)]
            ## reverse lookup to track which (index, start) derives
                from which templates
            ## needed to check for true paths
            read_tracker=defaultdict(set)
            for rstart, rtemplate, rindex in zip(read_start, read template, read index):
                read_tracker[(rstart, rindex)].add(rtemplate)
            ## keep only unique read_index, read_start pairs
            readlocs=np.zeros(shape=(template_count, max_start),
                dtype=bool)
            readlocs[read_index, read_start]=True
            read_start, read_index=np.where(readlocs.T)
            ## make a greedy assembly
            edge_in, edge_out, inscore=greedyAssembly(read_start, read_index, match, one_count, score_table,
                read_length, template_length)
            ## score the result
            true_exact_match, false_exact_match, true_path,
                false_path=pathScore(edge_in, edge_out, read_start,
                read_index, left_edge, right_edge, read_tracker)
            ## and output
            timediff=time.time( )−t0
            info=[template length, span_length, read_length, flip_rate, template_count, coverage, true_exact_match,
                false_exact match, true_path, false_path, timediff]
            print tabprint(info)
            sys.stdout.flush( )
many_windows_finite_coverage_counting
'''
Performs simulations testing the recovery of template
count over a template of many read lengths for a fixed
flip_rate,
and a range of read_lengths, and template counts,
and the number read lengths in the template
and a range of template coverage.
For speed, finds minimum cover in overlapping intervals of
length 2R and takes the maximum over all such windows.
We can do this because the maximum antichain
must be contained in an interval of length R
and must therefore be included in at least one interval.
The provides a speed advantage for long templates.
'''
import numpy as np
from support_functions import getRandomPatterns, getMatch, \
    getWordSpace, overlapMatch, tabprint
from hoperoft_karp import bipartiteMatch
import bisect
import sys
input parameters
seed=hash("This is not a seed.")
flip_rate=0.35

```
read_lengths=[10,20,30]
template_factors=(2**np.arange(1,5))
template_counts=2**np.arange(1,11)
coverages=np.arange(1, 11)
fixes a random seed
np.random.seed(seed)
headings=["template_length", "read_length", "flip_rate",
    "template_count", "coverage", "min_cover"]
print "\t".join(headings)
for each read length
for read_length in read_lengths:
    ## for each template factor
    for template_factor in template_factors:
        template_length=read_length*template_factor
        ## for each number of templates
        for template_count in template_counts:
            ## generate template patterns
            templates=getRandomPatterns(template_count, tem-
                plate_length, flip_rate)
            ## compute matches between templates over all pos-
                sible windows
            match=getMatch(templates, read_length)
            ## find space of unique reads
            word_space=getWordSpace(match)
            ## maximum read start position contained in the tem-
                plate
            max start=template length-read_length+1
            for ind, coverage in enumerate(coverages):
                num_reads=int(coverage*template_count*(float
                    (template_length)/float(read_length)))
                ## generate reads
                read_template=np.random.randint(0,    template_
                    count, num_reads)
                read_start=np.random.randint(0, max_start, num
                    reads)
                ## re-index reads from template space to word space
                ## word space assigns ambiguous reads to their least
                    template
                read_index=[word_space[x] for x in zip(read_tem-
                    plate, read_start)]
                ## keep only unique read_index, read_start pairs
                readlocs=np.zeros(shape=(template_count,
                    max_start), dtype=bool)
                readlocs[read index, read start]=True
                read_start, read index=np.where(readlocs.T)
                ## we will look at overlapping intervals of length 2R
                s=np.arange(0,    template_length-read_length,
                    step=read_length)
                e=s+2*read_length+1
                ## appropriate indices in read_starts
                A=[bisect.bisect_left(read_start, x) for x in s]
                B=[bisect.bisect_left(read_start, x) for x in e]
                ## set minimum cover to 0
                min_cover=0
                ## for each interval
                for (a,b) in zip(A, B):
                    ## get read starts and indices
                    rs=read_start[a:b]
                    ri=read_index[a:b]
                    ## get graph of all overlapping matching edges
                    overmatch_graph=overlapMatch(rs, ri, match,
                        read_length, template_length)
                    ## and all edges that fail to overlap
                    for i, j in zip(*np.where(np.less_equal.outer(rs+
                        read_length, rs))):
                        overmatch_graph[i].add(j)
                    ## compute bipartite matching
                    M, A, B=bipartiteMatch(overmatch_graph)
                    ## and take difference with vertex set for mini-
                        mum cover
                    mc=len(rs)-len(M)
                    ## update mincover to reflect maximum value
                    min_cover=max(mc, min_cover)
                ## and output the results
                info=[template_length, read_length, flip_rate, tem-
                    plate_count, coverage, min_cover]
                tabprint(info)
                sys.stdout.flush( )
many_windows_infinite_coverage
'''
Performs simulations testing the recovery of template count
and assembly
over a template of many read lengths
for a range of flip_rates, read_lengths, and template_counts
assuming exhaustive coverage
'''
#!/data/software/local/bin/python
import sys
import numpy as np
from support_functions import getRandomPatterns, tem-
    platesToWindows,
\
    generateCompleteDAG_trimmed, tabprint from hoper-
        oft_karp import bipartiteMatch
input parameters
read_lengths=[10, 20, 30]
template_factors=(2**np.arange(1,5))
flip_rates=np.linspace(0, 0.35, 8)[1:]
template_counts=2**np.arange(1,11)
seed=hash("This is not a random seed.")
fixes a random seed
np.random.seed(seed)
headings=['L', 'R', 'p', 'T', 'perfect_paths', 'min_cover']
print "\t".join(headings)
for read_length in read_lengths:
    ## for each read length, flip rate and number of templates
    for template_factor in template_factors:
        template_length=read length*template_factor
        for flip_rate in flip_rates:
            for template_count in template_counts:
                ## generate template patterns
                templates=getRandomPatterns(template_count,
                    template_length, flip_rate)
                ## generate reads as binary representations
                read=np.array(templatesToWindows(templates,
                    read_length))
                ## generate overlaps (read_length-1 windows)
                overlap=np.array(templatesToWindows(templates,
                    read_length-1))
                ## counts the number of overlap collisions for each
                    template at each window
                overlap_count=np.array([np.sum(np.equal.outer(x,
                    x), 0) for x in overlap.T]).T
                ## number of overlap collisions in each template
                collapse_count=np.sum(overlap_count>1, axis=1)
                ## the number of unambiguous paths
                ## (those with no overlap collisions at any position)
                perfect_paths=np.sum(collapse_count==0)
                ## generate bipartite graph from reads and overlaps
                    (trimmed of simple nodes)
                graph=generateCompleteDAG_trimmed(read, over-
                    lap)
                ## and determine maximal bipartite match to get
                    minimum vertex cover
```

```
        M, A, B=bipartiteMatch(graph)
        ## the size of the minimum cover
        ## equals the number of items lacking partners in the
            match
        min_cover=len(graph)-len(M)
        ## and report
        info=[template_length, read_length, flip_rate, tem-
            plate_count, perfect_paths, min_cover]
        print tabprint(info)
        sys.stdout.flush( )
support_functions
'''
A collection of function common to many of the simulation
tests. Includes methods for generating random template
patterns
and random reads from template patterns
as well as some of the directed graph functions
'''
import numpy as np
import heapq
import bisect
from collections import defaultdict, Counter
def tabprint(A):
    '''returns all elements of A, converted into strings and
joined by tabs.'''
    return "\t".join(map(str, A))
def toBinary(X):
    '''converts a bool array to its binary integer (or long)
representation'''
    return int((len(X)*'% d') % tuple(X[::-1]),2)
def bitCount(int_type):
    '''returns the number of bits that are on in the word'''
    return bin(int_type).count("1")
def toBitCount(inputArray):
    '''
    takes an array of binary ints and
    returns an array of the same size containing the bitcount
    '''
    ans=np.zeros_like(inputArray)
    for index, row in enumerate(inputArray):
        ans[index]=[bitCount(x) for x in row]
    return ans
def getRandomPatterns(number_of_templates, length_
of_template, probability_of_flip):
    '''generate random bit patterns'''
    return np.random.random(size=(number_of_templates,
length_of_template))<probability_of_flip
def templateToWindows(template, window_size):
    '''convert a template pattern into its sequence of window_
size subwords'''
    max_start=len(template)-window size+1
    return [toBinary(template[i:(i+window size)]) for i in
range(max_start)]
def templatesToWindows(templates, window_size):
    '''convert a set of template patterns into their sequence of
window_size subwords'''
    return [templateToWindows(template, window_size) for
template in templates]
def getMatch(templates, R, marks=None):
    '''
    function to determine exact agreement between all pairs
of templates
    starting at a position and extending up to some length.
    in particular:
    shape: template, template, position, window_size
    and match[T1, T2, P, W] returns the truth value for the
statement
    T1 and T2 match for every position on the window
P:(P+W)
    also set to accept a set of special marks.
    marks is None or a dictionary
    key is a position and marks[pos] are the mark values for
each template in order.
    for example, if each of four templates has a unique mark
at pos 10:
    marks[10]=[0,1,2,3]
    if there are two biallelic loci Aa and Bb with true phase
AB, ab, might have:
    marks[10]=[A, a, a, A]
    marks[70]=[B, b, b, B]
    '''
    T, L=templates.shape
    ## does a pair t1, t2 mismatch at a position p?
    mismatch_pos=np.zeros(shape=(T,T,L), dtype='bool')
    for i in range(T):
        mismatch_pos[i]=np.logical xor(templates[i], templates)
    ## if there are special marks:
    if marks !=None:
        ## then at each position:
        for pos in marks:
            markers=marks[pos]
            ## put a mismatch wherever markers disagree
            np.logical_or(mismatch_pos[:,:,pos], np.not_equal.ou-
                ter(markers, markers), out=mismatch_pos[:,:,pos])
    ## does a pair t1, t2 mismatch on a window p:(p+w)?
    mismatch=np.zeros(shape=(T,T,L, R+1), dtype='bool')
    for k in range(0, R):
        toEnd=L-k
        np.logical_or(mismatch[:, :, :toEnd, k], mismatch_
            pos[:, :, k:], out=mismatch[:, :, :toEnd, k+1])
    return np.logical not(mismatch)
def getWordSpace(match):
    '''
    At each position, converts from template index to word
index.
    if each word is unique at a position, then they are
identical. otherwise, each word is assigned its lowest index
template.
    This is necessary for handling collisions between reads
for indexing graph vertices.
    '''
    template_count=match.shape[0] ## number of templates
    read_length=match.shape[3]-1 ## length of read
    max_start=match.shape[2]-read_length+1 ## maximum
read start position
    word_space=np.zeros(shape=(template_count,
max_start), dtype=int)
    ## for each possible start position
    for pos in range(max_start):
        ## for each template
        for t in range(template_count):
            ## set word space to the least index with a match
            x=match[t, :, pos, -1]
            word_space[t, pos]=np.argmax(x)
    return word_space
def getOneCount(templates, read_length, dtype='int8'):
    '''
    Number of bits flipped to '1' for every template, every
        position, and every window up to the read length.
    Has shape: template, position, window_size and one_
        count[T, P, W] returns the number of flipped positions
        in the window P:(P+W) in template T.
    '''
    T, L=templates.shape
```

```
    one_count=np.zeros(shape=(T, L, read_length+1),
dtype=dtype)
    ## computed iteratively
    for k in range(0, read_length):
        toEnd=L-k
        one_count[:, :toEnd, k+1]=one_count[:, :toEnd, k]+tem-
            plates[:, k:]
    return one_count
def getScoreTable(read_length, flip_rate):
    '''
    Assigns a value to an edge based on the probability that
it is accidental.
    These values depend on the number of ones, the length of
the word,
    and the probability of a one.
    This function generates a lookup table that keeps the
values for:
    length of overlap, number of ones for a fixed flip rate.
    '''
    log p=np.log(flip_rate)
    log q=np.log(1-flip_rate)
    M=np.arange(read_length+1)[:, np.newaxis]
    K=np.arange(read_length+1)[np.newaxis, :]
    score_table=K*log p+(M-K)*log q
    return score_table
def generateCompleteDAG(read, overlap):
    '''
    function generates the enhanced directed acyclic graph
    assuming perfect data——all reads and all overlaps are
known.
    The primary DAG has vertices for each read
    and an edge from A to B if pos(B)=pos(A)+1
    and the reads agree on the overlap.
    The complete DAG has the same vertices,
    and an edge from A to B if there exists a path from A to B
in the primary DAG
    The reason for enhanced DAG is this:
    Applying bipartite matching to the primary DAG gives a
minimum vertex-disjoint cover.
    Applying bipartite matching to the enhanced DAG gives
a minimum vertex cover.
    '''
    graph=defaultdict(set)
    max_start=read.shape[1]-2
    ## iterate backwards from the next to last position to the
first
    for position in range(max_start, -1, -1):
        ## compute which overlaps agree
        overlap_match=np.equal.outer(overlap[:,   position+1],
            overlap[:, position+1])
        ## for all pairs that share an overlap
        for x,y in zip(*np.where(overlap_match)):
            source=(position, read[x, position]) ## define source
            target=(position+1, read[y, position+1]) ## and target
            ## to the source, add the target (and the target's targets)
            graph[source].update(graph[target])
            graph[source].add(target)
    return graph
'''
    Similar to the complete DAG
    but built from a primary DAG that is free of simple nodes.
    Y is a simple node if
    for X→Y→Z
    there is only one such X and Z and X has no other
out-edges.
    Then any path through Y must be from X and to Z
    and any path through X must continue through Z.
    So Y can be removed without changing the vertex cover.
    Repeat until there is no such Y in the graph.
'''
def generateCompleteDAG_trimmed(read, overlap):
    graph=defaultdict(set)
    max_start=read.shape[1]-2
    in_edge=defaultdict(set)
    out_edge=defaultdict(set)
    ## iterate backwards from the next to last position to the
first
    for position in range(max_start, -1, -1):
        ## compute which overlaps agree
        overlap_match=np.equal.outer(overlap[:,   position+1],
            overlap[:, position+1])
        ## for all pairs that share an overlap
        for x,y in zip(*np.where(overlap_match)):
            source=(position, read[x, position]) ## define source
            target=(position+1, read[y, position+1]) ## and target
            out_edge[source].add(target)
            in_edge[target].add(source)
    ## remove simple edges
    for x in in edge.keys( ):
        if len(in_edge[x])==1 and len(out_edge[x])==1:
            source, target=list(in_edge[x])[0], list (out_edge [x])
                [0]
            if len(out_edge[source])==1:
                out_edge[source].remove(x)
                in_edge[target].remove(x)
                out_edge[source].add(target)
                in_edge[target].add(source)
                del in_edge[x]
                del out_edge[x]:
    for x in in edge.keys( )
        if len(in_edge[x])==0:
            del in_edge[x]
    for x in out_edge.keys( ):
        if len(out_edge[x])==0:
            del out_edge[x]
    node_list=sorted(out_edge.keys( )[::-1]
    ## build graph
    for x in node list:
        graph[x].update(out_edge[x])
        for y in out_edge[x]:
            graph[x].update(graph[y])
    return graph
def generatePrimaryDAG(read, overlap):
    '''
    function generates the primary directed acyclic graph
    assuming perfect data——all reads and all overlaps are
known.
    The primary DAG has vertices for each read
    and an edge from A to B if pos(B)=pos(A)+1
    and the reads agree on the overlap.
    '''
    graph=defaultdict(set)
    max_start=read.shape[1]-2
    ## iterate backwards from the next to last position to the
first
    for position in range(max_start, -1, -1):
        ## compute which overlaps agree
        overlap_match=np.equal.outer(overlap[:,   position+1],
            overlap[:, position+1])
        ## for all pairs that share an overlap
        for x,y in zip(*np.where(overlap match)):
            source=(position, read[x, position]) ## define source
            target=(position+1, read[y, position+1]) ## and target
            graph[source].add(target)
```

```
    return graph
def overlapMatch(read_start, read_index, match, read_
length, template_length):
    '''
    First, assumes that read_starts are sorted. Safe in this
code.
    Uses bisect to make an index for the read_start positions.
    Then iterating over each position,
    checks for all overlaps in blocks to take advantage of
vector operations.
    Returns a list of all read pairs that overlap and agree on
that overlap.
    '''
    max_start=template_length−read_length+1
    ## number of reads
    num_nodes=len(read start)
    ## index into the start positions (assumed sorted)
    index_to_start=np.array([bisect.bisect_left(read_start, x)
for x in np.arange(template_length)]+[num_nodes])
    overmatch_graph=defaultdict(set)
    ## for each read start position in the template
    for a_pos in np.arange(max_start):
        ## get the upper and lower index bounds for a_pos
        low, high=index_to_start[a_pos:(a_pos+2)]
        ## get the upper index bound for possible overlaps
        end=index_to_start[a_pos+read_length]
        ## a is everything at this position (a_pos)
        ## b is everything from the next position on,
        ## that would overlap reads at this position.
        a_template=read_index[low:high]
        b_template=read_index[high:end]
        b_pos=read_start[high:end]
        overlap_length=read_length−b_pos+a_pos
        hasmatch=match[:,b_template,b_pos,overlap_length]
             [a_template]
        ## anything that has a match, goes into the list for i, j in
            zip(*np.nonzero(hasmatch)):
            overmatch_graph[low+i].add(high+j)
    return overmatch_graph
def pathScore(edge_in, edge_out, read_start, read_index,
left_edge, right_edge, read_tracker):
    '''
    Determine the number of exactly matched tag pairs.
    Of those, how many are tags from the same original
template ("true matches")?
    Of the true matches, how many admit a "true path"
    in which all the reads on the path could have derived from
the same initial template?
    True matched pairs that admit true paths
    are well-assembled templates in which all template infor-
mation,
    such as SNP phasing or intron exclusions,
    is recoverable from mutation pattern assembly alone.
    A true match with not true path correctly pairs the ends,
    but may have some errors in between.
    The function expects that the read_starts are sorted,
    so that out_edges always point to elements lower in the
list.
    '''
    num_nodes=len(edge_in)
    in_count=np.array([len(x) for x in edge_in]) ## number in
    out_count=np.array([len(x) for x in edge_out]) ## number
out
    path_start=np.where(in_count==0)[0] ## starts have no in
    path_end=np.where(out_count==0)[0] ## ends have no
out
    ## for each path start, add marks that are to the left of the
edge
    ## i.e. contain the left marker
    start_marks=[set( ) for_in range(num_nodes)]
    for pstart in path_start:
        if read_start[pstart]<left_edge:
            start_marks[pstart].add(pstart)
    ## propagate through the graph
    for source in range(num_nodes):
        for target in edge_out[source]:
            start_marks[target].update(start_marks[source])
    ## and out the end,
    ## track how many times a start node is seen an end node
    ## (beyond the right_edge, i.e. containing a right mark)
    start_counter=Counter( )
    for pend in path_end:
        if read_start[pend]>right_edge:
            for pstart in start_marks[pend]:
                start_counter[pstart]+=1
    def hasTruePath(tindex, node, pend):
        '''
        determines if there is a true path from node to pend,
        i.e. a path that traverses nodes supported by reads that are
            in the same template.
        Some nodes may be referred by multiple reads from
            different templates——
        if the mutation patterns are degenerate for more than a
            read length.
        '''
        if node==pend:
            return True
        elif tindex not in read_tracker[read_start[node], read_in-
            dex[node]]:
            return False
        else:
            for next_node in edge out[node]:
                if hasTruePath(tindex, next_node, pend):
                    return True
            return False
    ## now count up true and false exact matches and true
paths
    true_exact_match=0
    false_exact_match=0
    true_path=0
    false_path=0
    ## for each end
    for pend in path_end:
    ## if it is beyond the right edge (contains a right mark)
        if read_start[pend]>right_edge:
            ## does it have exactly one start?
            if len(start_marks[pend])==1:
                pstart=list(start marks[pend])[0]
                ## does that start have just one end?
                if start_counter[pstart]==1:
                    ## do they agree on template index?
                    if read_index[pstart]==read_index[pend]:
                        ## test for true path
                        tindex=read_index[pstart]
                        has_true_path=hasTruePath(tindex, pstart,
                            pend)
                        if has true path:
                            true_path+=1
                        else:
                            false_path+=1
                        true_exact_match+=1
                    else:
                        false_exact_match+=1
```

```
    return_true_exact_match, false_exact_match, true_path,
false_path
def scoredOutEdgeHeaps(read_start, read_index, match,
one_count, score_table, read_length, template_length):
    '''
    Function returns a list of ordered heaps of out edges for
each vertex.
    Two reads have an edge if they share an overlap, agree on
that overlap
    and are not at the exact same position.
    The score for an edge is the log likelihood of an accidental
overlap
    of that length and with that number of flipped bits.
    Used by greedy assembly.
    '''
    max_start=template_length-read_length+1
    ## number of reads
    num_nodes=len(read_start)
    ## index into the start positions (assumed sorted)
    index_to_start=np.array([bisect.bisect_left(read_start, x)
for x in np.arange(template_length)]+[num_nodes])
    ## for each node, make a heap to store out edges
    outedge_heaps=[[ ] for_in range(num_nodes)]
    ## for each read start position in the template
    for a_pos in np.arange(max_start):
        ## get the upper and lower index bounds for a_pos
        low, high=index_to_start[a_pos:(a_pos+2)]
        ## get the upper index bound for possible overlaps
        end=index_to_start[a_pos+read_length]
        ## a is everything at this position (a_pos)
        ## b is everything from the next position on,
        ## that would overlap reads at this position.
        a_template=read_index[low:high]
        b_template=read_index[high:end]
        b_pos=read_start[high:end]
        overlap_length=read_length-b_pos+a_pos
        hasmatch=match[:,b_template,b_pos,overlap_length]
            [a_template]
        for i, j in zip(*np.nonzero(hasmatch)):
            bits=overlap_length[j]
    ## bits of overlap
            flipped=one count[b_template[j], b_pos[j], bits]
    ## how many are on
            score=score_table[bits, flipped]
    ## lookup score
            heapq.heappush(outedge_heaps[low+i], (score, high+j))
    ## push into heap
    return outedge_heaps
def greedyAssembly(read_start, read_index, match, one_
count, score_table, read_length, template_length):
    '''
    Returns the edges of a greedy assembly.
    Iterate through the edges in order of least likely read
coincidence.
    Join an edge A to B if neither A nor B already have an out
(in) partner
    with a better score.
    '''
    num_nodes=len(read_start)
    ## getting edge out heaps
    outedge_heaps=scoredOutEdgeHeaps(read_start, read_
index, match, one_count, score_table, read_length, tem-
plate_length)
    ## keep the best in edge score for each vertex
    inscore=np.zeros(num_nodes, dtype=float)
    ## list of lists for storing edges
    edge_in =[list( ) for_in range(num_nodes)]
    edge_out=[list( ) for_in range(num_nodes)]
    ## build a heap for the vertices
    vertex heap=[ ]
    for i in range(num_nodes):
        try:
            ## ordered by the score of their top element
            item=(outedge_heaps[i][0][0], i)
            heapq.heappush(vertex_heap, item)
        except:
            ## should it exist
            continue
    ## then start working through the vertex heap
    while len(vertex heap)>0:
        ## find the out vertex with the best score
        score, out_vertex=heapq.heappop(vertex_heap)
        outheap=outedge_heaps[out_vertex]
        ## and then pop its heap to get all its partners with that
            best score
        foundPartner=False
        while len(outedge_heaps[out_vertex])>0:
            if outheap[0][0]==score: ##
    if best element has score
                in_score, in_vertex=heapq.heappop(outheap) ## pop it off
                    the heap
                ## check if its a good score for the in vertex
                if score <=inscore[in_vertex]:
                    foundPartner=True ##
    found a partner
                    edge_in[in vertex].append(out_vertex) ##
    add the edges
                    edge_out[out_vertex].append(in_vertex)
                    inscore[in_vertex]=score ##
    and record the score
            else:
                break
        ## if the vertex did not find a partner, it returns to the
            vertex heap
        ## with its best score.
        if not foundPartner:
            try:
                item=(outedge heaps[out_vertex][0][0], out_vertex)
                heapq.heappush(vertex_heap, item)
            except:
                continue
    return edge_in, edge_out, inscore
```

REFERENCES

1. McCloskey M L, Stoger R, Hansen R S, & Laird C D (2007) Encoding PCR products with batch-stamps and barcodes. *Biochemical genetics* 45(11-12):761-767.
2. Miner B E, Stoger R J, Burden A F, Laird C D, & Hansen R S (2004) Molecular barcodes detect redundancy and contamination in hairpin-bisulfite PCR. *Nucleic acids research* 32(17):e135.
3. Casbon J A, Osborne R J, Brenner S, & Lichtenstein C P (2011) A method for counting PCR template molecules with application to next-generation sequencing. *Nucleic acids research* 39(12):e81.
4. Fu G K, Hu J, Wang P H, & Fodor S P (2011) Counting individual DNA molecules by the stochastic attachment of diverse labels. *Proceedings of the National Academy of Sciences of the United States of America* 108(22):9026-9031.
5. Islam S, et al. (2014) Quantitative single-cell RNA-seq with unique molecular identifiers. *Nature methods* 11(2):163-166.

6. Jabara C B, Jones C D, Roach J, Anderson J A, & Swanstrom R (2011) Accurate sampling and deep sequencing of the HIV-1 protease gene using a Primer ID. *Proceedings of the National Academy of Sciences of the United States of America* 108(50):20166-20171.
7. Kivioja T, et al. (2012) Counting absolute numbers of molecules using unique molecular identifiers. *Nature methods* 9(1):72-74.
8. Hiatt J B, Pritchard C C, Salipante S J, O'Roak B J, & Shendure J (2013) Single molecule molecular inversion probes for targeted, high-accuracy detection of low-frequency variation. *Genome research* 23(5):843-854.
9. Kinde I, Wu J, Papadopoulos N, Kinzler K W, & Vogelstein B (2011) Detection and quantification of rare mutations with massively parallel sequencing. *Proceedings of the National Academy of Sciences of the United States of America* 108(23):9530-9535.
10. Schmitt M W, et al. (2012) Detection of ultra-rare mutations by next-generation sequencing. *Proceedings of the National Academy of Sciences of the United States of America* 109(36):14508-14513.
11. Hicks J, Navin N, Troge J, Wang Z, & Wigler M (2012) Varietal counting of nucleic acids for obtaining genomic copy number information. (Patent)
12. Keith J M, et al. (2004a) Algorithms for sequence analysis via mutagenesis. *Bioinformatics* 20(15):2401-2410.
13. Keith J M, et al. (2004b) Unlocking hidden genomic sequence. *Nucleic acids research* 32(3):e35.
14. Mitchelson K R (2011) Sequencing of difficult DNA Regions by SAM sequencing. *Methods in molecular biology* 687:75-88.
15. Sipos B, Massingham T, Stutz A M, & Goldman N (2012) An improved protocol for sequencing of repetitive genomic regions and structural variations using mutagenesis and next generation sequencing. *PloS one* 7(8):e43359.
16. Shortle D & Botstein D (1983) Directed mutagenesis with sodium bisulfite. *Methods in enzymology* 100:457-468.
17. Dilworth R P (1950) A Decomposition Theorem for Partially Ordered Sets. *Ann Math* 51(1):161-166.
18. König D (1931) Graphen and matrizen. *Mat. Fiz. Lapok* 38:116-119.
19. Hoperoft J & Karp R (1973) An $n^{5/2}$ Algorithm for Maximum Matchings in Bipartite Graphs. *SIAM Journal on Computing* 2(4):225-231.
20. Alberts B (1994) *Molecular biology of the cell* (Garland Pub., New York) 3rd Ed pp xliii, 1294, 1267 p.
21. Narzisi G & Mishra B (2011) Scoring-and-unfolding trimmed tree assembler: concepts, constructs and comparisons. *Bioinformatics* 27(2):153-160.
22. Bransteitter R, Pham P, Scharff M D, & Goodman M F (2003) Activation-induced cytidine deaminase deaminates deoxycytidine on single-stranded DNA but requires the action of RNase. *Proceedings of the National Academy of Sciences of the United States of America* 100(7):4102-4107.
23. Krueger F & Andrews S R (2011) Bismark: a flexible aligner and methylation caller for Bisulfite-Seq applications. *Bioinformatics* 27(11):1571-1572.
24. Otto C, Stadler P F, & Hoffmann S (2012) Fast and sensitive mapping of bisulfite-treated sequencing data. *Bioinformatics* 28(13):1698-1704.
25. Krueger F, Kreck B, Franke A, & Andrews S R (2012) DNA methylome analysis using short bisulfite sequencing data. *Nature methods* 9(2):145-151.

What is claimed:

1. A method for determining the number of nucleic acid molecules (NAMs) in a group of NAMs, comprising
   i) obtaining an amplified and mutagenized group of NAMs that was produced by
      a. subjecting the group of NAMs to a chemical mutagenesis which mutates only select nucleic acid bases in the group of NAMs at a rate of 10% to 90% thus forming a group of mutagenized NAMs (mNAMs), and
      b. amplifying the group of mNAMs;
   ii) obtaining sequences of the mNAMs in the group of amplified mNAMs; and
   iii) counting the number of different sequences obtained in step (ii) to determine the number of unique mNAMs in the group of mNAMS,
   thereby determining the number of NAMs in the group of NAMs.

2. The method of claim 1, wherein obtaining sequences in step (ii) comprises obtaining composite sequences produced by assembling sequence reads of the mNAMs by
   a) aligning the sequence reads according to matching mutation patterns in overlaps of the sequence reads, thereby obtaining composite sequences, and
   b) mapping the composite sequences; and
   wherein step (iii) comprises counting the number of jointly overlapping different composite sequences obtained in step (ii).

3. The method of claim 1, wherein a sub-group of NAMs in the group of NAMs is determined to have substantially the same nucleotide sequence,
   wherein the sub-group of NAMs is determined to have nucleotide sequences that are at least 95, 96, 97, 98, 99, 99.1, 99.2, 99.3, 99.4, 99.5, 99.6, 99.7, 99.9, or 99.9% identical; or
   wherein the nucleotide sequences of a sub-group of NAMs comprise a stretch of consecutive nucleotides having a sequence which includes at least two mutable positions and is i) identical to the sequence of a stretch of consecutive nucleotides within another NAM within the sub-group of NAMs, or ii) determined to have at least 95, 96, 97, 98, 99, 99.1, 99.2, 99.3, 99.4, 99.5, 99.6, 99.7, 99.9, or 99.9% identical to the sequence of a stretch of consecutive nucleotides within another NAM within the sub-group of NAMs.

4. The method of claim 1, wherein the counting comprises counting the number of different sequences that are determined to have substantially the same sequence except for their mutable positions, thereby determining the number of NAMs in the group of NAMs that had substantially the same sequence; or
   wherein the counting comprises counting the number of different sequences which lack substantially the same sequence in any stretch including at least two mutable positions, thereby determining the number of NAMs without substantially the same sequence in the group of NAMs.

5. The method of claim 1, wherein
   a) the mutagenesis is by cytosine deamination,
   b) each mutable position of the NAMs comprises a cytosine and the cytosine (C) is mutated to a uracil (U) or a thymine (T),
   c) each NAM in the group of NAMs has a unique primer at its 5' end and another unique primer at its 3' end,
   d) the NAM is within a mixture of DNA or RNA extracted from a cell, wherein the DNA or RNA extracted from the cell has been fragmented,
   e) the NAM is a DNA molecule, or an RNA molecule,
   f) one or more NAMs in the group of NAMs has a length of one sequencing read length,
   g) one or more NAMs in the group of NAMs has a length of two or more sequencing read lengths, and/or
   h) the number of NAMs in the group of NAMs is about 2, 3, 4, 5, 6, 7, 8, 9, 10, or 10-10000, wherein if the number of NAMs in the group of NAMs is greater than 10000, then diluting the group of NAMs.

6. The method of claim 1, further comprising the step of tagging each NAM or copy thereof, wherein the tag lacks a nucleotide that is mutable by the mutagenesis.

* * * * *

UNITED STATES PATENT AND TRADEMARK OFFICE
CERTIFICATE OF CORRECTION

| | | |
|---|---|---|
| PATENT NO. | : 11,008,606 B2 | Page 1 of 1 |
| APPLICATION NO. | : 15/515913 | |
| DATED | : May 18, 2021 | |
| INVENTOR(S) | : Wigler et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 590 days.

Signed and Sealed this
Eighteenth Day of February, 2025

Coke Morgan Stewart
*Acting Director of the United States Patent and Trademark Office*

SEQUENCE LISTING

```
<160> NUMBER OF SEQ ID NOS: 4

<210> SEQ ID NO 1
<211> LENGTH: 35
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (1)..(35)
<223> OTHER INFORMATION: m3c or m5c
<220> FEATURE:
<221> NAME/KEY: modified_base
<222> LOCATION: (35)..(35)
<223> OTHER INFORMATION: phosphorothioated

<400> SEQUENCE: 1
acactctttc cctacacacg acgctcttcc gatct                          35

<210> SEQ ID NO 2
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (1)..(32)
<223> OTHER INFORMATION: m3c or m5c
<220> FEATURE:
<221> NAME/KEY: modified_base
<222> LOCATION: (32)..(32)
```

```
<223> OTHER INFORMATION: phosphorothioated

<400> SEQUENCE: 2
gatcggaaga gcggttcagc aggaatgccg ag                                32

<210> SEQ ID NO 3
<211> LENGTH: 35
<212> TYPE: DNA
<213> ORGANISM: Artificial Sequence
<220> FEATURE:
<223> OTHER INFORMATION: Primer

<400> SEQUENCE: 3
acactctttc cctacacacg acgctcttcc gatct                             35

<210> SEQ ID NO 4
<211> LENGTH: 32
<212> TYPE: DNA
<213> ORGANISM: Artificial Sequence
<220> FEATURE:
<223> OTHER INFORMATION: Primer

<400> SEQUENCE: 4
gatcggaaga gcggttcagc aggaatgccg ag                                32
```